US012688394B2

(12) United States Patent
Sakhinana et al.

(10) Patent No.:  US 12,688,394 B2
(45) Date of Patent:        Jul. 21, 2026

(54) SYSTEM AND METHOD FOR MOLECULAR PROPERTY PREDICTION USING EDGE CONDITIONED IDENTITY MAPPING CONVOLUTION NEURAL NETWORK

(71) Applicant: Tata Consultancy Services Limited, Mumbai (IN)

(72) Inventors: Sagar Srinivas Sakhinana, Pune (IN); Venkata Sudheendra Buddhiraju, Pune (IN); Venkataramana Runkana, Pune (IN); Sri Harsha Nistala, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1229 days.

(21) Appl. No.: 17/450,666

(22) Filed: Oct. 12, 2021

(65) Prior Publication Data

US 2023/0045690 A1      Feb. 9, 2023

(30) Foreign Application Priority Data

Jul. 16, 2021    (IN) .............................. 202121032176

(51) Int. Cl.
G06N 3/04        (2023.01)
G06F 9/50        (2006.01)
            (Continued)

(52) U.S. Cl.
CPC ............. G06N 3/04 (2013.01); G06F 9/5044 (2013.01); G06F 9/546 (2013.01);
            (Continued)

(58) Field of Classification Search
CPC . G06N 3/04; G06N 3/042; G06N 3/08; G16C 20/30; G16C 20/70; G06F 18/2155; G06F 9/5044; G06F 9/546
See application file for complete search history.

(56) References Cited

U.S. PATENT DOCUMENTS 11,216,620 B1 *   1/2022   Jin ........................ G06F 40/216
11,526,766 B2 *   12/2022  Song .................. G06Q 20/4016
            (Continued)

FOREIGN PATENT DOCUMENTS

CN        112862092        5/2021

OTHER PUBLICATIONS

Longa, "Pytorch Geometric tutorial: Aggregation Functions in GNNs", https://www.youtube.com/watch?v=tGXovxQ7hKU&t= 5s, Mar. 21, 2021, screen printout pp. 1-2 (Year: 2021).*
            (Continued)

*Primary Examiner* — Tamara T Kyle
*Assistant Examiner* — William Wong
(74) *Attorney, Agent, or Firm* — FINNEGAN, HENDERSON, FARABOW, GARRETT & DUNNER LLP

(57)        ABSTRACT

This disclosure relates generally to system and method for molecular property prediction. Typically, message-pooling mechanism employed in molecular property prediction using conventional message passing neural networks (MPNN) causes over smoothing of the node embeddings of the molecular graph. The disclosed system utilizes edge conditioned identity mapping convolution neural network for the message passing phase. In message passing phase, the system computes an incoming aggregated message vector for each node of the plurality of nodes of the molecular graph based on encoded message received from neighboring nodes such that encoded message vector is generated by fusing a node information and an connecting edge information of the set of neighboring nodes of the node. The incoming aggregated message vector is utilized for computing updated hidden state vector of each node. A discriminative graph-level vector representation is computed by
            (Continued)

pooling the updated hidden state vectors from all the nodes of the molecular graph.

17 Claims, 4 Drawing Sheets

(51) Int. Cl.

| | |
|---|---|
| *G06F 9/54* | (2006.01) |
| *G06F 18/214* | (2023.01) |
| *G06N 3/042* | (2023.01) |
| *G06N 3/08* | (2023.01) |
| *G16C 20/30* | (2019.01) |
| *G16C 20/70* | (2019.01) |

(52) U.S. Cl.
CPC ......... *G06F 18/2155* (2023.01); *G06N 3/042* (2023.01); *G06N 3/08* (2013.01); *G16C 20/30* (2019.02); *G16C 20/70* (2019.02)

(56) References Cited

U.S. PATENT DOCUMENTS

| | | | | |
|---|---|---|---|---|
| 2018/0268220 | A1* | 9/2018 | Lee ........................ | G06V 10/44 |
| 2019/0139622 | A1* | 5/2019 | Osthege ................... | G16B 5/20 |
| 2019/0229820 | A1* | 7/2019 | Scaglione .............. | H04B 17/23 |
| 2019/0272468 | A1* | 9/2019 | Feinberg ................ | G16B 15/30 |
| 2019/0303535 | A1* | 10/2019 | Fokoue-Nkoutche ....................... | |
| | | | | G06F 17/16 |
| 2020/0285944 | A1* | 9/2020 | Lee ........................ | G06F 18/24 |
| 2021/0398621 | A1* | 12/2021 | Stojevic ................. | G16C 10/00 |
| 2022/0383992 | A1* | 12/2022 | Triendl ................. | G06N 3/045 |

OTHER PUBLICATIONS

Simonovsky, Martin et al., "Dynamic Edge-Conditioned Filters in Convolutional Neural Networks on Graphs", Neural and Evolutionary Computing, Aug. 2017, Arxiv, https://arxiv.org/pdf/1704.02901. pdf, 12 pages.

Withnall, M. et al., "Building attention and edge message passing neural networks for bioactivity and physical-chemical property prediction", Journal of Cheminformatics, Jan. 2020, vol. 12 (1), Springer, http//jcheminf.biomedcentral.com/track/pdf/10.1186/s13321-019-0407-y.pdf, 18 pages.

Yang, Yulei et al., "NENN: Incorporate Node and Edge Features in Graph Neural Networks", Asian Conference on Machine Learning, 2020, vol. 129, PMLR, http://proceedings.mlr.press/v129/yang20a. pdf, 16 pages.

Huang, Wenbing et al., "Tackling Over-Smoothing for General Graph Convolutional Networks", Machine Learning, Mar. 2021, Arxiv, https://arxiv.org/pdf/2008.09864.pdf, 14 pages.

Gong, Liyu et al., "Exploiting Edge Features for Graph Neural Networks", Machine Learning, Jan. 2019, Arxiv, https://arxiv.org/ pdf/1809.02709.pdf, 10 pages.

Klicpera, Johannes et al., "Predict Then Propagate: Graph Neural Networks Meet Personalized Pagerank", Machine Learning, Feb. 2019, Arxiv, https://arxiv.org/pdf/1810.05997.pdf, 15 pages.

Grattarola, Daniele et al., "Graph Neural Networks in TensorFlow and Keras with Spektral", Computational Intelligence Magazine, Jan. 2021, IEEE, https://ieeexplore.ieee.org/stamp/stamp.jsp? arnumber=9321429, 8 pages.

Do[a,b,*], Tien Huu et al., "Graph Convolutional Neural Networks with Node Transition Probability-based Message Passing and DropNode Regularization", Machine Learning, Mar. 2021, Arxiv, https://arxiv. org/pdf/2008.12578.pdf, 39 pages.

* cited by examiner

Graph

Computation Graph for Target Node : A

Message Passing : Leaves ——▶ Root Node

ACCESS, VIA ONE OR MORE HARDWARE PROCESSORS, A DATABASE COMPRISING A PLURALITY OF MOLECULAR GRAPHS ASSOCIATED WITH A PLURALITY OF MOLECULES AND A PLURALITY OF LABELS INDICATIVE OF CHEMICAL PROPERTIES OF THE PLURALITY OF THE MOLECULAR GRAPHS, EACH MOLECULAR GRAPH OF THE PLURALITY OF MOLECULAR GRAPHS COMPRISES A PLURALITY OF NODES AND A PLURALITY OF EDGES CONNECTING THE PLURALITY OF NEIGHBORING NODES ⟋ 402

LEARN, VIA THE ONE OR MORE HARDWARE PROCESSORS, A MAPPING FROM THE PLURALITY OF MOLECULAR GRAPHS TO THE SET OF LABELS BY A MOLECULAR PROPERTY PREDICTION NEURAL NETWORK FUNCTION TO PROGNOSTICATE THE PROPERTIES OF A MOLECULAR GRAPH FROM AMONGST THE PLURALITY OF MOLECULAR GRAPHS BY COMPUTING A GRAPH-LEVEL VECTOR REPRESENTATION OF THE MOLECULAR GRAPH USING AN EI-MPNN

COMPUTE AN INCOMING AGGREGATED MESSAGE VECTOR FOR EACH NODE OF THE PLURALITY OF NODES OF THE MOLECULAR GRAPH BASED ON A PLURALITY OF ENCODED MESSAGES RECEIVED FROM A SET OF NEIGHBORING NODES OF THE EACH NODE, WHEREIN EACH ENCODED MESSAGE VECTOR IS GENERATED BY FUSING A NODE INFORMATION AND AN CONNECTING EDGE INFORMATION OF THE SET OF NEIGHBORING NODES OF THE NODE ⟋ 406

⟋ 404

COMPUTE ITERATIVELY AN UPDATED HIDDEN STATE VECTOR OF EACH NODE IN A PLURALITY OF PRE-DETERMINED NUMBER OF ITERATIONS FROM INCOMING AGGREGATED MESSAGE VECTOR AND A HIDDEN STATE OF SAID NODE, WHEREIN THE HIDDEN STATE OF THE NODE IS OBTAINED FROM A PREVIOUS ITERATION ⟋ 408

CALCULATE A DISCRIMINATIVE GRAPH-LEVEL VECTOR REPRESENTATION BY POOLING THE UPDATED HIDDEN STATE VECTORS OF THE PLURALITY OF NODES, WHEREIN THE GRAPH-LEVEL VECTOR REPRESENTATION IS A CHARACTERISTIC REPRESENTATION OF THE MOLECULAR GRAPH ⟋ 410

APPLY A LINEAR LAYER ON DISCRIMINATIVE GRAPH-LEVEL VECTOR REPRESENTATION TO COMPUTE THE MOLECULAR PROPERTIES, VIA THE ONE OR MORE HARDWARE PROCESSORS ⟋ 412

FIG. 4
400

SYSTEM AND METHOD FOR MOLECULAR PROPERTY PREDICTION USING EDGE CONDITIONED IDENTITY MAPPING CONVOLUTION NEURAL NETWORK

PRIORITY CLAIM

This U.S. patent application claims priority under 35 U.S.C. § 119 to: India Application No. 202121032176, filed on Jul. 16, 2021. The entire contents of the aforementioned application are incorporated herein by reference.

TECHNICAL FIELD

This disclosure relates generally to molecular property predictions, and more particularly to system and method for molecular property prediction using edge conditioned identity mapping convolution neural network.

BACKGROUND

The prediction of molecular properties is a fundamental task in the field of drug discovery. The prediction can be done by a variety of computational methods that significantly accelerate the overall process of finding better drug candidates in a time and cost-efficient manner. Machine learning technique, in specific, supervised learning on drug-like potential molecules has remarkable applications for use in more effective drug discovery. It provides substantial prospects in diminishing the computational complexity which is a key desideratum for prognostication of molecular properties and aid in billion price tag cost reduction of developing a potential drug for treatment.

Typically, Convolution Neural Networks (CNNs) and its variant structured neural network architectures obtain dimensionality reduction and extract dominant features for molecular properties prediction tasks by performing spatial convolutions on Euclidean domains. The CNNs input have a regular and grid-like structure. This restriction hampers the utilization of CNN's to numerous scientific disciplines, where irregular graph structure or manifold data are commonly accessible.

To deal with the all too often non-grid-like data structures, graph Neural Networks (GNNs), are popularly been looked upon as a noteworthy modeling framework, to perform inference on graph data. GNNs learn hidden representations of nodes, subgraphs, and the whole input graph by synchronous message-aggregation from node neighborhood by following through computational graph of the nodes. These learned hidden representations are rotation and translation invariant. Graph Neural Network (GNN) or its subsequent improvised variants are effective algorithms for learning the discriminative node embeddings of the arbitrary sized, graph-structured data by utilizing the relational inductive biases that are shared across the non-Euclidean graph domain. These low-dimensional representations of each node entities serve as feature inputs for graph-pooling, to evaluate the graph-level embeddings and aid in graph based inductive (semi-supervised) or rather for transductive (supervised) learning tasks.

In a known study, the one-hop node neighborhood permutation-invariant (independent on the arbitrary ordering of nodes) message-aggregation (spatial graph convolution) was utilized to transform the node representations, and a Graph Convolutional Network (GCN) was presented. The algorithm exemplified state-of-the-art results in metrics concerning the semi-supervised classification tasks. Another study revealed GCNs ability to relational reasoning. Yet another study presented a coalesce framework through a function-setting invariant message-passing and read-out phase. Each node in the graph sends neural messages to its local-node neighborhood based on its hidden states and overhauls its hidden states established on the aggregated message received from its immediate adjoining neighbors through the edge-type connecting them as overlapping partitions of the original graph. Still another study presented a unique and distinct neural message-aggregation and node embeddings update algorithmic approach to evaluate a representation of the entire input complex topology molecular graphs. By leveraging message passing neural networks (MPNNs) on open-sourced datasets, a state-of-the-art performance was achieved and a benchmark for predicting molecular properties was established.

Recent advances improvise the performance of GCNs include and not limited to the gating, skip connection, jumping connection, attention mechanism, sampling strategy, hierarchical representation, generative models, adversarial attack and defenses, etc. Notable work leveraging GCNs are in social science, knowledge graph, recommendation systems, etc. Chemical graph theory treats drug-like organic molecules as static graphs. Recent works on drug-generation and property prediction tasks, include hierarchical message-passing schemes on molecular graphs, benchmarking platform for molecular generation models, hierarchical generation of chemical graphs, multi-objective molecule generation, organic chemical reaction prediction, and for predicting synthesis routes for molecules generation. It is desired to introduce alternative models in the MPNN foster family set that can complement with a decrease in time complexity, thereby yielding a considerable drop in resource consumption over previous MPNNs for computation of low dimensional node embeddings in comparison with the baselines.

SUMMARY

Embodiments of the present disclosure present technological improvements as solutions to one or more of the above-mentioned technical problems recognized by the inventors in conventional systems. For example, in one embodiment, a processor implemented method for molecular property prediction using edge conditioned identity mapping convolution neural network is provided. The method includes accessing, via one or more hardware processors, a database comprising a plurality of molecular graphs associated with a plurality of molecules and a plurality of labels indicative of chemical properties of the plurality of the molecular graphs, each molecular graph of the plurality of molecular graphs comprises a plurality of nodes and a plurality of edges connecting the plurality of neighboring nodes. The method further includes learning, via the one or more hardware processors, a mapping from the plurality of molecular graphs to the set of labels by a molecular property prediction neural network function to prognosticate the properties of a molecular graph from amongst the plurality of molecular graphs, wherein predicting the properties of the molecular graph comprises computing a graph-level vector representation of the molecular graph using an Edge-Information Fused Message Passing Neural Network (EI-MPNN). Computing the graph-level vector representation for the molecular graph comprises computing an incoming aggregated message vector for each node of the plurality of nodes of the molecular graph, the incoming aggregated message vector for each node is computed based on a plurality of encoded messages received from a set of neighboring nodes of the each node, wherein each encoded message vector is generated by fusing a node information and an connecting edge information of the set of neighboring nodes of the node; computing iteratively an updated hidden state vector of each node in a plurality of pre-determined number of iterations from incoming aggregated message vector and a hidden state of said node, wherein the hidden state of the node is obtained from a previous iteration; and calculating a discriminative graph-level vector representation by pooling the updated hidden state vectors of the plurality of nodes, wherein the graph level vector representation is a characteristic representation of the molecular graph. Furthermore, the method includes applying a linear layer function on discriminative graph-level vector representation to compute the molecular properties, via the one or more hardware processors.

In another aspect, a system for molecular property prediction using edge conditioned identity mapping convolution neural network is provided. The system includes a memory storing instructions; one or more communication interfaces; and one or more hardware processors coupled to the memory via the one or more communication interfaces, wherein the one or more hardware processors are configured by the instructions to access a database comprising a plurality of molecular graphs associated with a plurality of molecules and a plurality of labels indicative of chemical properties of the plurality of the molecular graphs, each molecular graph of the plurality of molecular graphs comprises a plurality of nodes and a plurality of edges connecting the plurality of neighboring nodes. The one or more hardware processors coupled to the memory via the one or more communication interfaces to learn a mapping from the plurality of molecular graphs to the set of labels by a molecular property prediction neural network function to prognosticate the properties of a molecular graph from amongst the plurality of molecular graphs, wherein predicting the properties of the molecular graph comprises computing a graph-level vector representation of the molecular graph using an Edge-Information Fused Message Passing Neural Network (EI-MPNN). To computing the graph-level vector representation for the molecular graph, the one or more hardware processors are configured by the instructions to compute an incoming aggregated message vector for each node of the plurality of nodes of the molecular graph, the incoming aggregated message vector for each node is computed based on a plurality of encoded messages received from a set of neighboring nodes of the each node, wherein each encoded message vector is generated by fusing a node information and an connecting edge information of the set of neighboring nodes of the node; compute iteratively an updated hidden state vector of each node in a plurality of pre-determined number of iterations from incoming aggregated message vector and a hidden state of said node, wherein the hidden state of the node is obtained from a previous iteration; and calculate a discriminative graph-level vector representation by pooling the updated hidden state vectors of the plurality of nodes, wherein the graph level vector representation is a characteristic representation of the molecular graph. The one or more hardware processors coupled to the memory via the one or more communication interfaces to apply a linear layer function on the discriminative graph-level vector representation to compute the molecular properties.

In yet another aspect, there are provided one or more non-transitory machine-readable information storage mediums comprising one or more instructions which when executed by one or more hardware processors cause accessing, via one or more hardware processors, a database comprising a plurality of molecular graphs associated with a plurality of molecules and a plurality of labels indicative of chemical properties of the plurality of the molecular graphs, each molecular graph of the plurality of molecular graphs comprises a plurality of nodes and a plurality of edges connecting the plurality of neighboring nodes. The method further includes learning, via the one or more hardware processors, a mapping from the plurality of molecular graphs to the set of labels by a molecular property prediction neural network function to prognosticate the properties of a molecular graph from amongst the plurality of molecular graphs, wherein predicting the properties of the molecular graph comprises computing a graph-level vector representation of the molecular graph using an Edge-Information Fused Message Passing Neural Network (EI-MPNN). Computing the graph-level vector representation for the molecular graph comprises computing an incoming aggregated message vector for each node of the plurality of nodes of the molecular graph, the incoming aggregated message vector for each node is computed based on a plurality of encoded messages received from a set of neighboring nodes of the each node, wherein each encoded message vector is generated by fusing a node information and an connecting edge information of the set of neighboring nodes of the node; computing iteratively an updated hidden state vector of each node in a plurality of pre-determined number of iterations from incoming aggregated message vector and a hidden state of said node, wherein the hidden state of the node is obtained from a previous iteration; and calculating a discriminative graph-level vector representation by pooling the updated hidden state vectors of the plurality of nodes, wherein the graph level vector representation is a characteristic representation of the molecular graph. Furthermore, the method includes applying a linear layer function on the discriminative graph-level vector representation to compute the molecular properties, via the one or more hardware processors.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 4 is a flow diagram illustrating a method for molecular property prediction in accordance with some embodiments of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Message Passing Neural Networks (MPNN) framework merges several distinct and unique contemporary models that exist in the literature. The MPNNs are an abstraction of a non-spectral approach based graph convolution neural networks. The MPNNs operate on undirected chemical graphs, $\mathcal{G}^{\mathcal{M}} = (\mathcal{V}^{\mathcal{M}}, \mathcal{E}^{\mathcal{M}})$.

Let $\mathcal{N}^{\mathcal{M}}$ ($|\mathcal{V}^{\mathcal{M}}|$) denote the number of nodes and $E^{\mathcal{M}}$ ($|\mathcal{E}^{\mathcal{M}}|$) represents the number of edges for a homogenous chemical graph, $\mathcal{G}^{\mathcal{M}}$. $\mathcal{G}^{\mathcal{M}}$ is described by a set of node features, $$N^{\mathcal{M}} \in R^{|\mathcal{V}^{\mathcal{M}}| \times \mathbb{C}}, N_i^{\mathcal{M}} \in R^{1 \times \mathbb{C}} \forall i \in \mathcal{V}^{\mathcal{M}}$$

and edge features $$e_{ij}^{\mathcal{M}} \in R^{|\mathbb{E}^{\mathcal{M}}| \times \mathbb{Z}}, \forall (i, j) \in \mathcal{E}^{\mathcal{M}}.$$

Here, i & j$\in \mathcal{V}^{\mathcal{M}}$ refer to the neighboring nodes of the chemical graph and are connected by an arbitrary edge, $(i,j) \in \mathcal{E}^{\mathcal{M}} \leftrightarrow (j, i) \in \mathcal{E}^{\mathcal{M}}$, $\forall j \in \mathcal{N}$ (i). The chemical graph connectivity $\mathcal{G}^{\mathcal{M}} = (\mathcal{V}^{\mathcal{M}}, \mathcal{E}^{\mathcal{M}})$ is given by the adjacency matrix, $$\mathcal{G}_{\mathcal{A}}^{\mathcal{M}}.$$

Molecules are represented as annotated undirected chemical graphs. The atoms are considered to be the nodes of the chemical graphs. The bonds connecting adjacent atoms in the chemical graphs correspond to edges. The MPNN framework is leveraged in this particular scientific discipline for mathematical modeling of the drug-like organic molecules. It helps to gain insight and assists in the description of the chemical graph's topology into a characteristic representation of the entire chemical graphs to later aid in the molecular property prediction task. Based on the graph's connectivity, an incident edge in between two neighboring atoms in the chemical compound (or nodes in a chemical graph) acts as both arriving and departing edge tagged by the same label (bond type).

Figures 1, 2:
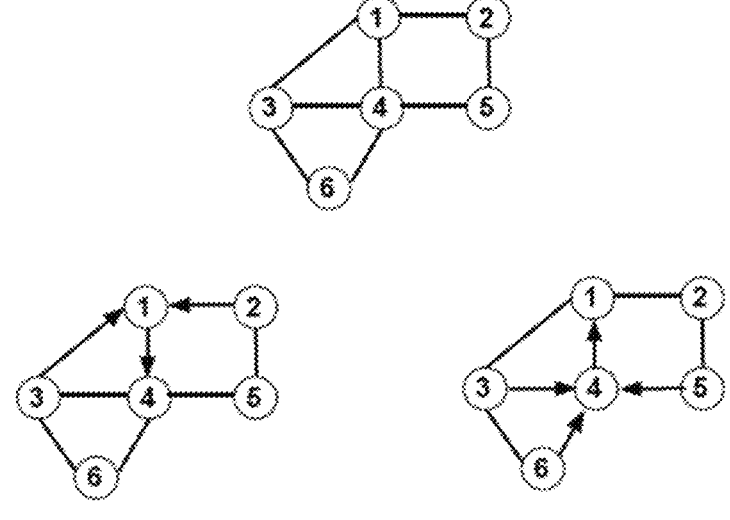
FIG. 1 illustrates a representation of message passing phase of a conventional message passing neural network (MPNN).
FIG. 2 illustrates a representation of readout phase of a conventional message passing neural network (MPNN).

The MPNNs forward pass consists of two phases—a message passing phase (illustrated in FIG. 1) and a readout phase (illustrated in FIG. 2). The message passing phase generates neural messages and update node representations by aggregating encoded information of node's embeddings from confined graph neighborhood. A permutation invariant readout phase is leveraged to perform graph pooling. Readout phase function takes an adjacency matrix $$\mathcal{G}_A^{\mathcal{M}}$$

as input and satisfies the following property, $$\mathcal{F}(P\mathcal{G}_A^{\mathcal{M}}P^T) = \mathcal{F}(\mathcal{G}_A^{\mathcal{M}}).$$

Here, P is a permutation matrix. The message propagation utilizes the distinct message generating functions acting on the undirected chemical graph topology $$M_{in}^f \text{ and } M_{out}^f$$

represents the universal function approximator for the generation of neural messages received through a particular edge type and propagated from the same edge-type between the nodes of the chemical graphs, respectively. Based on the direction of the edge under consideration, that particular transformation function is put into operation on the edge, $$e_{ji}^{\mathcal{M}}.$$

The MPNNs forward pass communicates messages as described by a computational graph for every target node from the bottom (leaf) node to the top (root) node by iterating for T computational time steps. These outgoing messages are evaluated for every edge by transforming the source node's hidden state according to the edge feature vector.

Identical edge-type incident on different node neighbors, which is characterized by distinct edge feature vectors share with the same instance of the message generating neural-network function. Each node in the molecular graph aggregates neural messages (message-pooling operation) from its local T-hop neighbors, as determined from $$\mathcal{G}_A^{\mathcal{M}}$$

and the received messages are perceived by the target node by performing mathematical computations to update its hidden representation. This message-passing scheme assists in learning effective discriminative hidden representations of the nodes in the chemical graphs, by adopting a Back-propagation through time (BPTT) learning algorithm for training the MPNNs framework when solved for graph-based inductive learning tasks. The MPNNs are synchronous message-passing systems. They update all messages in parallel. In the end, each edge between the vertices in the chemical graph have messages evaluated in both directions from the source to sink and contrariwise. The message passing phase is described by utilizing a message generating function, $M^f$, and node-embedding update neural network function, $V^f$. $M^f$ and $V^f$ might take possession of diverse in specific to be at variance with function settings. During the span of the message passing phase, the node-level embedding $$h_i^t$$

of every unique vertex in the molecular graph as given by its computational graph are overhauled and assembled on structural and feature information embedded messages $$m_i^{t+1},$$

received from its one-hop neighbors as depicted by, $$m_i^{t+1} = \sum_{j \in N(i)} M^f\!\left(h_j^t, \, e_{ji}^M\right) \qquad (1)$$

$$h_i^{t+1} = V^f\!\left(h_i^t, \, m_i^{t+1}\right) \qquad (2)$$

Here, $$\sum_{j \in N(i)}$$

depicts the aggregation of neural-information embedded messages over the local one-hop neighborhood of the node, i.e $\in \mathcal{V}^M$ in the chemical graph, $\mathcal{G}^M$. Here, $h_i$ is learned with the MPNN model parameters through a representative function of the entire input graph when solved for addressing supervised graph regression tasks such as molecular graph property prediction. The readout phase of the MPNN framework performs graph-pooling through set-pooling approach by determining a discriminative graph embedding for the entire input molecular graph by utilizing a differentiable node-reordering invariant neural network function, $R^f$ according to, $$\hat{y} = R^f\!\left(\{h_i^T \mid i \in \mathcal{V}^M(\mathcal{G}^M)\}\right).$$

$M^f$, $V^f$, and $R^f$ are differentiable neural network functions and have learnable parameters. Mini-Batching with an MPNN with batch size as a hyper-parameter results in the faster training and augments performance of the graph-based deep learning algorithm. It is viable here in this context as it initiates and propagates neural messages across several molecular graphs with varying numbers of vertices $|\mathcal{V}^M|$ and $|\mathcal{E}^M|$. The feature representation of the vertices in the molecular graph, $\mathcal{G}^M$ is denoted by, data.x. data.edgeindex describes the edge indices of source and sink vertices of the edge under consideration and vice-versa. data.edgeattr represents the static edge attributes. data.y is the pre-determined DFT-evaluated properties (ground-truth) for the chemical graphs. The discrepancy between the MPNN model output (estimated) and the true values are measured by the mean-squared error loss function for this graph-based supervised regression task. The Edge-Conditioned Convolution Networks (ECCN) Is described by, $$h_i^{t+1} = \Lambda h_i^t + \sum_{j \in N(i)} h_j^t \cdot \Omega_\Lambda\!\left(e_{ij}^M\right)$$

Here, $\Omega_\Lambda$ denotes a multilayer perceptron, parameterized by $\Lambda$. The aggregated vector message perceived by the sink node, i is described by $$m_i^{t+1} = \sum_{j \in N(i)} h_j^t \cdot \Omega_\Lambda\!\left(e_{ij}^M\right).$$

The MPNN framework message-generating neural-network function is described by, $$M^f\!\left(h_j^t, \, e_{ij}^M\right) = h_j^t \cdot \Omega_\Lambda\!\left(e_{ij}^M\right).$$

The vertex update function is described by, $$V^f\!\left(h_i^t, \, m_i^{t+1}\right) : GRU\!\left(h_i^t, \, m_i^{t+1}\right).$$

Here, GRU is a known Gated Recurrent Unit. The hidden state of the previous state is given by, $$v^f\!\left(h_i^t, \, m_i^{t+1}\right) : GRU\!\left(h_i^t, \, m_i^{t+1}\right).$$

Here, n denotes the total number of nodes in the chemical graphs in a given batch size. $d_m$ & $d_h$ are the characteristic dimension of neural messages and node attributes respectively. Here, the reset gate, $$R_t, Z_t, h_i^t, \tilde{h}_i^t$$

are evaluated as, $$R_t = \sigma\!\left(m_i^{t+1} W_r + h_i^t W_{rh} + b_r\right), \qquad (3)$$

$$Z_t = \sigma\!\left(m_i^{t+1} W_z + h_i^t W_{zh} + b_z\right), \qquad (4)$$

$$\tilde{h}_i^t = \tanh\!\left(m_i^{t+1} W_{\tilde{h}} + (R_t \odot h_i^t) W_{hh} + b_h\right) \qquad (5)$$

$$h_i^{t+1} = Z_t \odot h_i^t + (1 - Z_t) \odot \tilde{h}_i^t \qquad (6)$$

Here, $W_r$, $W_z$, $W_{\tilde{h}} \in \mathbb{R}^{d_m \times d_h}$, $W_{rh}$, $W_{zh}$, $W_{hh} \in \mathbb{R}^{d_h \times d_h}$ are the weight parameters, $b_r$, $b_z$, $b_h \in \mathbb{R}^{1 \times d_h}$ are the bias.

The graph-level global pooling neural network is evaluated as $$\hat{y} = R^f\!\left(\{h_i^T \mid i \in \mathcal{V}^M(\mathcal{G}^M)\}\right) : Set2Set\!\left(\{h_i^T \mid i \in \mathcal{V}^M(\mathcal{G}^M)\}\right) \qquad (7)$$

---

Algorithm: Hypergraph message passing neural network

1: Input Feature Training set: data.x, data.edgeindex, data.edgeattr
2: Input Target Label : data.y
3: Regularization Term: Apply dropout on data.x, data.edgeindex, & data.edgeattr
4: Message-Passing Phase
5: for t T do
6: Forward Pass & Vertex Update: Perform HyperGraph Convolution
7: end for -continued

| Algorithm: Hypergraph message passing neural network |
| --- |
| 8: Read out Operation: Apply Set2Set Algorithm |
| 9: Linear Layer |
| 10: Return Graph level output : Predict DFT target properties |

The MPNN however leads to over-smoothing of learnable embeddings for vertices with higher valency. Various embodiments described herein provides a method and system for molecular property prediction using MPNN in a manner that can alleviate the expressivity of the GCN by leveraging the edge-information in the graph structure of the molecules. Further, the disclosed method and system preventing over-smoothing of learnable embeddings for vertices with higher valency, as will be explained further in the description below.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Figure 3:
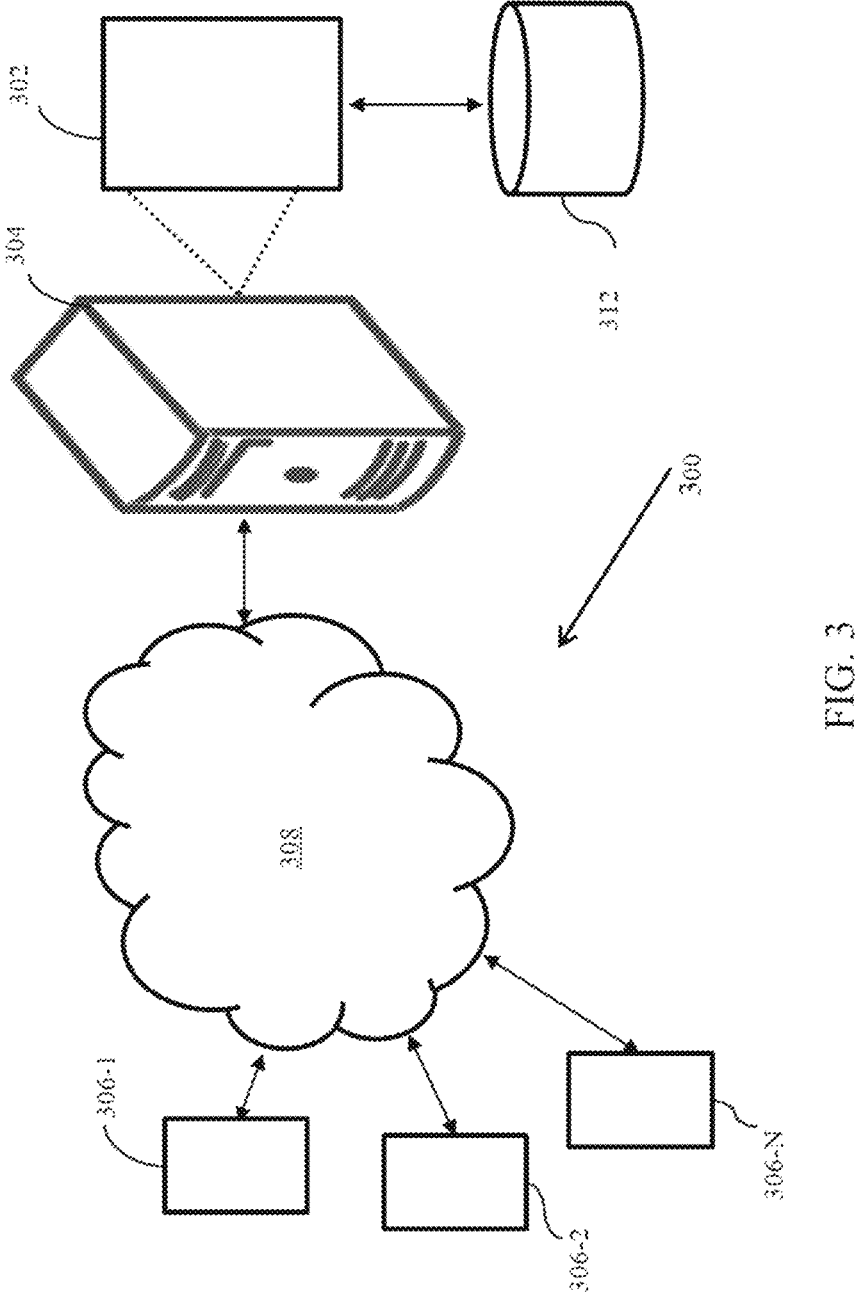
FIG. 3 illustrates a network implementation of a system for molecular property prediction according to some embodiments of the present disclosure.
Figure 5:
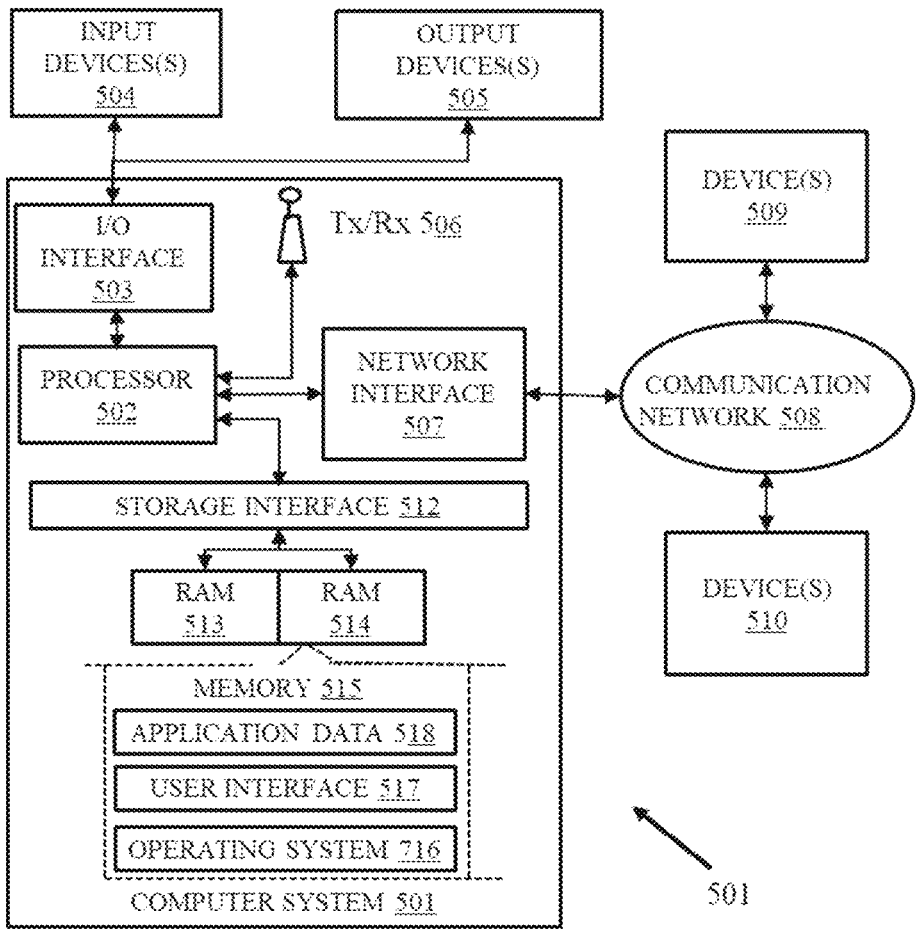
FIG. 5 is a block diagram of an exemplary computer system for implementing embodiments consistent with the present disclosure.

Referring now to the drawings, and more particularly to FIG. 3 through 5, where similar reference characters denote corresponding features consistently throughout the figures, there are shown preferred embodiments and these embodiments are described in the context of the following exemplary system and/or method.

FIG. 3 illustrates an example network implementation 300 of a system 302 for molecular property prediction using MPNN in accordance with example embodiment of present disclosure. The disclosed system provides a supervised learning on drug-like potential molecules for use in effective drug discovery. It provides substantial prospects in diminishing the computational complexity which is a key desideratum for prognostication of molecular properties and aid in billion price tag cost reduction of developing a potential drug for treatment. The system 302 enables design variants for injective multi-set neural-network functions for message-generation and message pooling mechanism on local-graph neighborhood following the computational graph of each node in the given molecular graphs of bounded tree-width. Herein, the term 'local-graph neighborhood' of a node refers to one or more neighboring nodes od said node. Accordingly, the terms 'local-graph neighborhood', 'local-neighborhood', and neighboring nodes may be used interchangeably throughout the description.

The proposed variants are resilient to noise by learning to adapt to kingpin on the task-relevant fragment of the molecular graphs at varying receptive fields, locality, and depth to augment the discriminative power of node & graph-level embeddings. The novel designs of message-passing pipeline variants comprises of message-passing, vertex update and graph-pooling modules and are jointly learned in an end-to-end framework and augment the graph-level prediction tasks accuracy by taking into account the structure of the graph. The proposed novel designs of message-passing pipeline variants augment the graph-level prediction tasks accuracy by taking into account the structure of the graph.

Although the present disclosure is explained considering that the system 302 is implemented on a server, it may be understood that the system 302 may also be implemented in a variety of computing systems 304, such as a laptop computer, a desktop computer, a notebook, a workstation, a cloud-based computing environment and the like. It will be understood that the system 302 may be accessed through one or more devices 306-1, 306-2 . . . 306-N, collectively referred to as devices 306 hereinafter, or applications residing on the devices 306. Examples of the devices 306 may include, but are not limited to, a portable computer, a personal digital assistant, a handheld device, a smartphone, a tablet computer, a workstation and the like. The devices 306 are communicatively coupled to the system 302 through a network 308.

In an embodiment, the network 308 may be a wireless or a wired network, or a combination thereof. In an example, the network 308 can be implemented as a computer network, as one of the different types of networks, such as virtual private network (VPN), intranet, local area network (LAN), wide area network (WAN), the internet, and such. The network 306 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 308 may include a variety of network devices, including routers, bridges, servers, computing devices, storage devices. The network devices within the network 308 may interact with the system 302 through communication links.

As discussed above, the system 302 may be implemented in a computing device 304, such as a hand-held device, a laptop or other portable computer, a tablet computer, a mobile phone, a PDA, a smartphone, and a desktop computer. The system 302 may also be implemented in a workstation, a mainframe computer, a server, and a network server. In an embodiment, the system 302 may be coupled to a data repository, for example, a repository 312. The repository 312 may store data processed, received, and generated by the system 302. In an alternate embodiment, the system 302 may include the data repository 312.

The network implementation 300 supports various connectivity options such as BLUETOOTH®, USB, ZigBee® and other cellular services. The network environment enables connection of devices 306 such as Smartphone with the server 304, and accordingly with the database 312 using any communication link including Internet, WAN, MAN, and so on. In an exemplary embodiment, the system 302 is implemented to operate as a stand-alone device. In another embodiment, the system 302 may be implemented to work as a loosely coupled device to a smart computing environment.

FIG. 4 illustrates a flow chart of a method 400 for molecular property prediction using edge conditioned identity mapping convolution neural network, in accordance with an example embodiment of present disclosure. Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 400 are described with help of system 102. However, the operations of the method 400 can be described and/or practiced by using any other system.

At step 402 of method 400, a database comprising a plurality of molecular graphs associated with a plurality of molecules is accessed. The database further includes a plurality of labels indicative of chemical properties of the plurality of the molecular graphs. Each molecular graph of the plurality of molecular graphs includes a plurality of nodes and a plurality of edges connecting a plurality of neighboring nodes from amongst the plurality of nodes. For example, the database may include annotated independent and identically distributed molecular graphs.

$$D^M = (G_1^M, y_1^M), (G_1^M, y_1^M) \dots (G_{|D^M|}^M, y_{|D^M|}^M)$$

Here, $$y_i^M$$

are the associated chemical properties corresponding to the molecular graph, $$\mathcal{G}_A^M.$$

The objective of the graph-based molecular property prediction framework is by operating on the topology of the molecular graphs described by a set of node features, $\mathcal{N}^M \in \mathbb{R}^{|\mathcal{V}^M| \times \mathcal{C}}$ and static edge features, $$e_{ij}^M \in \mathbb{R}^{|\mathcal{E}^M| \times z}, \forall (i, j) \in \mathcal{E}^M$$

is to learn a novel mapping $$f : \mathcal{G}^M \to h_k^M, \forall k \in \mathcal{V}^M \to h_\mathcal{G}^M \to y_i^M$$

that maps molecular graphs structure to the set of labels.

$$h_k^M$$

is the learned hidden representation vector of node k. Here, $$y_i^M$$

denotes the target molecular properties.

At 404, the method 400 includes learning a mapping from the plurality of molecular graphs to the set of labels by a molecular property prediction neural network function to prognosticate the properties of a molecular graph from amongst the plurality of molecular graphs using an Edge-Information Fused Message Passing Neural Network (EI-MPNN). Herein, predicting the properties of the molecular graph includes computing a graph-level vector representation of the molecular graph using the EI-MPNN. The method for computing the graph-level vector representation of the molecular graph using the EI-MPNN is described with reference to steps 406-410.

Various embodiments of the disclosed method provides variants of differentiable neural-network functions to operate on low tree-width molecular graphs for generation of local graph structure and feature information encoded messages ($\mathcal{MG}$) and the vertex update mechanism ($\mathcal{UPD}$) for learning discriminative node embeddings using EI-MPNN. These learned hidden representations are rotation and translation invariant. These low-dimensional representations of each node entity, serve as feature inputs for graph-pooling. In an embodiment, the method also includes defining a variant for edge information fused global graph-pooling set-aggregator operator, $R^f$. The mathematical function $\mathcal{MG}$, takes as input the set of node and edge attributes, the graph, $\mathcal{G}^M$, connectivity, described by the adjacency matrix $$\mathcal{G}_A^M.$$

$\mathcal{AGG}$ denotes the message-aggregation mechanism from local-graph neighborhood (or the set of neighboring nodes). Further, the method includes a sum-pooling approach for message-aggregation from the set of neighboring nodes. That is, permutation invariance to nodes ordering is obtained by summation of local messages to a message vector at the sink node. $\mathcal{UPD}$ takes as input the aggregated message from the local-graph neighborhood and the node-level embeddings of the graph at a previous layer (or iteration). Here, $m_{\mathcal{N}(i)}$ represents the aggregated neural message from node, i's local-graph neighborhood, E.

$$m_{\mathcal{N}(i)} \neq m_{\mathcal{N}(j)} \leftrightarrow \mathcal{N}(i) \neq \mathcal{N}(j), (j, i) \in E \qquad (8)$$

$$m_{\mathcal{N}(i)} = \mathcal{AGG}(\mathcal{MG}\{h_j^{(l)}, e_{ji}^M, \forall j \in \mathcal{N}(i)\})$$

Here, the learnable parameters are shared across the nodes of the graph. The message-passing update phase is described below, $$h_i^{(l+1)} = \mathcal{UPD}(h_i^{(l)}, \mathcal{AGG}(\mathcal{MG}\{h_j^{(l)}, e_{ji}^M, \forall j \in \mathcal{N}(i)\})) \qquad (9)$$

$$h_i^{(l+1)} = \mathcal{UPD}(h_i^{(l)}, m_{\mathcal{N}(i)}^{(l)}) \qquad (10)$$

Here, l refers to the layer. The MPNN pipeline operates on annotated molecular graphs in two subsequent phases, the message passing phase characterized by $\mathcal{MG}$, $\mathcal{AGG}$, $\mathcal{UPD}$ neural-network functions and the readout phase characterized by global-pooling operator, $R^f$, see algorithm 1.

The selection of a function setting for a set-aggregator, $R^f$ is of paramount importance, as it should allow invariance to the MPNN model output to the order of selection of the node-level embeddings. The objective of a set pooling function, $R^f$ is to map the graph's node-level embeddings $$\left\{ h_i^T, \dots, h_{|\mathcal{V}^\mathcal{M}|}^T \right\}$$

to a graph-level embedding $$h_\mathcal{G}^\mathcal{M},$$

which characterizes the entire input graph. The graph-level representation is acquired by utilizing a novel variant of set2set algorithm that takes into account the structure of the molecular graph similar to graph clustering or coarsening pooling operations. It leverages recurrent neural networks with extended memory and attention mechanism to pool the abstract, low-level representations of the nodes in the graph. It is driven by a mechanism of iterative content-based attention and is chosen to work on a sample of node representations. It implements a linear projection to every tuple $$\left( h_i^T, x_i^\mathcal{M} \right) \cdot x_i^\mathcal{M} \left( h_i^0 = x_i^\mathcal{M} \right)$$

denotes the feature vector of the node, i. Then the sample of projected tuples is fed as input to the algorithm. It's iterated for M computational steps. Then the graph level embedding determined, $$h_\mathcal{G}^\mathcal{M},$$

from the graph-topology aware variant of set2set algorithm is immutable to the selection order of the tuples T. In this set-based graph-pooling approach, the attention-based aggregations are described below, $$Q_t = LSTM(O_{t-1}, Q_{t-1}) \tag{11}$$

$$S_{i,t} = f_a \left( e_{ij}^\mathcal{M} . \Theta \left[ h_j^T \| x_i^\mathcal{M} \right], Q_t \right), , \forall\, i \in v^\mathcal{M} \tag{12}$$

$$a_{i,t} = \frac{\exp(s_{i,t})}{\sum_{j \in v^\mathcal{M}} \exp(s_{j,t})}, \forall\, i \in v^\mathcal{M} \tag{13}$$

$$O_t = \sum_{i \in v^\mathcal{M}} a_{i,t} \left( e_{j,i}^\mathcal{M} \cdot \Theta \left[ h_i^T \| x_i^\mathcal{M} \right] \right) \tag{14}$$

which are iterated for t=1 . . . , M steps. $Q_t$ denotes a query vector, $f_a$ denotes the attention function & $a_{i,t}$ represents the attention coefficients of node, i evaluated at each iteration step, t. Here, $\Theta$ is a linear layer & $O_t$ denotes the weighted sum of the low-level abstract representations of the nodes in the chemical graph. The graph-level embedding is determined by, $$h_M^* = O_1 \odot O_2 \odot \dots \odot O_M.$$

This embedding $$h_\mathcal{G}^\mathcal{M}$$

is fed through a downstream multi-layer perceptron neural network to predict the target molecular properties of the chemical graphs. Here, $\odot$ denotes element-wise multiplication.

As mentioned previously, the disclosed message-passing pipeline variants in the EI-MPNN foster family are trained by learning end-to-end. They are effective algorithms for learning the discriminative node embeddings of the arbitrary sized, non-linear chemical graph-structured data by utilizing the relational inductive biases that are shared across the non-Euclidean graph domain. These pipeline formalism variants driven by inductive learning tasks are leveraged for the molecular graphs properties prediction.

Algorithm 1: Disclosed Method of Synchronous Message Passing Schemes

---

Require: Molecular Graph , Node Feature & Static Edge-feature Matrix
Ensure: T-hop, local-graph neighborhood, message-aggregation
    for t ∈ [T] do
        # Propagate messages
        for i ∈ ( ) do
          for j ∈ (i) do $$\phi_{j \to i}^{(t)} = \mathcal{MG} \left( h_j^{(t-1)}, e_{ji}^\mathcal{M} \right)$$

end for
        end for
        # Update vertex hidden states
        for i ∈ ( ) do $$h_i^{(t)} = \mathcal{UPD} \left( h_i^{(t-1)}, \mathcal{AGG}_{j \in N_i} \phi_{j \to i}^{(t)} \right)$$

end for
    end for
Graph-level Embedding $$h_{\mathcal{G}^\mathcal{M}} = R^f \left( \left\{ h_i^T \right\}, \forall\, i \in \mathcal{V}^\mathcal{M}(\mathcal{G}^\mathcal{M}) \right)$$

Return Graph-level embedding, hGM.

---

The node-level feature information of the undirected molecular graph, $\mathcal{G}^\mathcal{M}$ is described by the real-valued feature matrix, $\mathcal{N}^\mathcal{M} \in \mathbb{R}^{|\mathcal{V}^\mathcal{M}| \times \mathcal{C}}$. To alleviate overfitting, $$\mathcal{G}_A^\mathcal{M} = \mathcal{G}_A^\mathcal{M} + I_N$$

represent the adjacency matrix with non-zero value entries in the diagonal due to the added value of self-loops. The self-loop are added to dwindle the influence of periphery nodes of the molecular graphs and to effectively perform graph convolution by weighing in on the local graph-neighbors feature and structure information.

$$\hat{\mathcal{G}}_A^M = \tilde{D}^{-1/2} \tilde{\mathcal{G}}_A^M \tilde{D}^{-1/2}$$    5 is the symmetric-normalized adjacency matrix accompanied by self-loops. The diagonal degree matrix, with the added self-loops, is described by, $$\tilde{D}_{ij} = \sum_i \tilde{\mathcal{G}}_{A\ ii}^M \delta_{ij}.$$

is the reciprocal of the diagonal matrix, $\tilde{D}$. A Graph Convolutional Network (GCN) performs convolution in the spatial domain, a simple variant of message-passing algorithm utilized for semi-supervised classification task. In the case of two-hop neighborhood message-passing scheme, its equation is described by, $$Y^z = \text{softmax}\left(\hat{\mathcal{G}}_A^M ReLU\left(\hat{\mathcal{G}}_A^M N^M W_0\right) W_1\right).$$

Here, $W_0$ and $W_1$ represent the learnable weight matrices. With two GCN-layers, only neighbors in the two-hop neighborhood is considered for message-pooling operation. $Y^z \in \mathbb{R}^{|V^M| \times c_y}$ denotes the predicted node labels for classification tasks. Here, $c_y$ denotes the number of classes, a type or category for a node-level based classification task solved by utilizing a negative log-likelihood loss. GCN node-wise formulation is described by the below equation.

$$h_i' = W \sum_{j \in N(i) \cup \{i\}} \frac{h_j}{\sqrt{\tilde{d}_j \tilde{d}_i}}$$

Here, W is the trainable weight parameter. 40

To alleviate the expressivity of the GCN and to leverage the edge information of the graph structure, the disclosed method utilizes an Edge-Conditioned Graph Convolutional operator, as described with reference to multiple embodiments below.

At 406, the method 400 includes computing an incoming aggregated message vector for each node of the plurality of nodes of the molecular graph. The incoming aggregated message vector for each node is computed based on a plurality of encoded messages received from a set of neighboring nodes of each node. Each encoded message vector is generated by fusing a node information and a connecting edge information of the set of neighboring nodes of the node. At 308, the method 300 includes computing iteratively an updated hidden state vector of each node in a plurality of pre-determined number of iterations from incoming aggregated message vector and a hidden state of said node. Herein, the hidden state of the node for a current iteration is obtained from a previous iteration from amongst the plurality of pre-determined number of iterations.

In an example embodiment, the updated hidden state vector $$\left(h_i^{(t+1)}\right)$$

of each node (i) is computed by transforming the hidden state vector $$\left(h_i^t\right)$$

of previous iteration step of each node (i) by using a feed-forward neural-network function $\Gamma_\Theta$. The input to the feed-forward neural-network function includes a summation of a linear transformation of the node (i) hidden state vector $$\left(h_i^t\right)$$

with a first trainable weight matrix, $\Theta_1$ and the aggregated-message vector from the set of neighboring nodes. In the present embodiment, each of the plurality of encoded messages comprises a normalized neural-message vector. The normalized neural-message vector from each neighboring node of the set $$\left(h_j^t\right)$$

of neighboring moves is determined by a ratio of a summation of hidden state vector of each node in the set of neighboring nodes (j), and a linearly transformed static edge feature vector altered by a second trainable weight matrix, $\Theta_2$ and a square-root of a product of a degree of the node (i) and the set of neighboring nodes (j) with added self-loops. Herein, in calculating the degree of each node, an arbitrary edge that starts and terminates at the same node is considered, such an edge is termed as a self-loop of said node. It is described in its node-wise formulation as:

$$h_i' = \Gamma_\Theta\left((1 + \epsilon)W_0 h_i + \sum_{j \in N(i)} \frac{1}{\sqrt{\hat{d}_j \hat{d}_i}}\left(h_j + W_1 e_{j,i}^M\right)\right) \quad (15)$$

Here, $h_i$ is the representation vector of node, i at previous layer. $d_i$ is the degree of a node, i with added self-loop. $W_0$ & $W_1$ are trainable weight matrices that apply a linear transformation to feature and static edge feature vectors respectively. Here, $\Gamma_\Theta$ denotes a neural network, i.e. an MLP parameterized by $\Theta$. $\epsilon$ denotes the epsilon value, $e^{-7}$.

In another embodiment, the EI-MPNN comprises an Edge-Conditioned Identity Mapping Convolution Network (EC-IMCN). The EC-IMCN aids in inductive learning tasks by incorporating the edge-information of the graph topology and prevents over-smoothing of learnable low-level representations for nodes with higher valency. It prevents diffusion of node embeddings to its local sizeable-graph neighborhood. It is described by, $$h_i' = W_1 h_i + m_{N(i)} \quad (16)$$

In the present embodiment, the updated hidden state vector $$\left(h_i^{(t+1)}\right)$$

17 or each node (i) is computed by transforming the previous hidden state vector of the node (i) by performing a summation operation on a linear transformation of the node(i) hidden state vector with the trainable weight matrix, $\Theta_1$ and the aggregated neural-message vector from the set of neighboring nodes. Herein, the aggregated neural-message vector is determined by computing a product of transformed strength of an identity mapping to allow a gated aggregated neural-information flow from the set of neighboring nodes. Further herein, the gated aggregated neural-information flow is determined by a summation of a weighted product of a less-discriminative aggregated message-vector $$\sum\nolimits_{j \in N(i)} h_j^t \Omega_\Lambda\left(e_{ij}^{\mathcal{M}}\right)$$

with $(1-\alpha)$ and a weighted product of an initial residual aggregated neural-message vector $$\sum\nolimits_{j \in N(i)} h_j^{(0)} \Omega_\Lambda\left(e_{ij}^{\mathcal{M}}\right)$$

with $\alpha$(a learnable gating scalar value). The less-discriminative and the initial residual aggregated neural-message vector are determined by a sum-message pooling operation. The less-discriminative message-vector is determined by a product of the transformed edge-vector with the neighboring node (j), hidden state, and is described by $$h_j \Omega_\Lambda\left(e_{ij}^{\mathcal{M}}\right).$$

The initial residual neural-message vector is determined by a product of the transformed edge-vector with the neighboring node j, feature vector, and is described by $$h_j^0 \Omega_\Lambda\left(e_{ij}^{\mathcal{M}}\right).$$

the transformed edge-vector comprises the output of a feed-forward neural network function, $\Omega_\Lambda$, which takes as input the static-edge feature vector, $$e_{ij}^{\mathcal{M}}.$$

Mathematically, the aggregated message-vector, $m_{\mathcal{N}(i)}$ determined by sum-pooling operation on the local-graph neighborhood is described by, $$m_{\mathcal{N}(i)} = \tag{17}$$

$$\left((1-\alpha)\sum\nolimits_{j \in N(i)} h_j^t \Omega_\Lambda\left(e_{ji}^{\mathcal{M}}\right) + \alpha \sum\nolimits_{j \in N(i)} h_j^{(0)} \Omega_\Lambda\left(e_{ji}^{\mathcal{M}}\right)\right)((1-\beta)I + \beta W_2)$$

Here, $W_1$ and $W_2$ are the trainable weight matrices.

$$e_{ij}^{\mathcal{M}}$$

18 denotes the static feature vector of the edge connecting the neighboring nodes, (j, i). It describes the edge type and spatial information.

$$h_j^{(0)}$$

represents the feature information vector of the node, j. Here, $\alpha$ models the strength of the initial residual aggregated neural-message vector from local-graph neighbors, $$\sum\nolimits_{j \in N(i)} h_j^{(0)} \Omega_\Lambda\left(e_{ij}^{\mathcal{M}}\right),$$

$\alpha$ & $(1-\alpha)$ serves the role as the gating vectors by combining information from the less-discriminative aggregated single message-vector, $$\sum\nolimits_{j \in N(i)} h_j^t \Omega_\Lambda\left(e_{ij}^{\mathcal{M}}\right)$$

with the initial residual aggregated neural-message vector. Here, $\beta$ models the strength of the identity mapping to the corresponding learnable weight matrix, W2. Here, $\Omega_\Lambda$ denotes a multi-layer perceptron, parameterized by $\Lambda$. 1 is the identity matrix.

As previously identified, GCN has an inherent limitation to leverage a larger-neighborhood of the graph to bring forth a transformation of abstract representations of the node to embed local-graph neighborhood information. The message-pooling mechanism would cause over smoothing of the node embeddings of the graph by operating on a stack of GCN layers. It has lost information of the node feature attributes, despite increment in the receptive field due to deeper graph convolutional networks. It is partly attributed due to the diffusion of the abstract representations of each node with its local-graph neighbors. GCN coincides and intersects with the graph's random walk limit distribution as the number of GCN layers in the stack escalate. The limit distribution is a characteristic feature of the entire graph and thereby it does not account for the root node of the random walks. A node-ordering invariant aggregation function that maps a set of node-level embeddings ($\{h_i, \forall i \in \mathcal{V}(\mathcal{G})\}$) to a graph-level embedding $h_\mathcal{G} = \phi\{h_i, \forall i \in \mathcal{V}(\mathcal{G})\}$ or that maps node-level neural-messages $\{m_{ji}, \forall j \in \mathcal{N}(i)\}$ to a single message-vector $m_{\mathcal{N}(i)} = \phi\{m_{ji}, \forall j \in \mathcal{N}(i)\}$ by performing a message-pooling operation, can be approximated by a neural-network architecture by abiding with the universal set pooling function approximator as described by, $$h_\mathcal{G} = MLP_X\left(\sum\nolimits_{j \in N(i)} MLP_\psi(h_i)\right), \forall i \in \mathcal{V}(\mathcal{G}), \text{ and} \tag{18}$$

$$m_{\mathcal{N}(i)} = MLP_X\left(\sum\nolimits_{j \in N(i)} MLP_\psi(m_{ji})\right), \forall j \in \mathcal{N}(i) \tag{19}$$

Here, $$\hat{A} = (D+1)^{-\frac{1}{2}}(A+I)(D+I)^{-\frac{1}{2}}$$

is the normalized adjacency matrix. Here the graph connectivity matrix, A is added with self-loops between a node and itself, and $g(\hat{A})$ is the function of $\hat{A}$.

The likelihood of teleporting to the root node assists us to retain the root node feature vector obligations and allows to trade-off with the information aggregation from larger local-graph node-adaptive receptive field to learn discriminative node level embeddings. The anti-oversmoothing approximate edge-information fused personalized propagation of neural predictions layer is computed as, $$h_i^{(0)} = \sum\nolimits_{j \in N(i)} \Theta_1 e_{j,i} \cdot f_i \tag{20}$$

$$h_i^t = (1-\alpha)GRU\left((1+\epsilon)h_i^{(t)}, \sum\nolimits_{j \in N(i)} \frac{1}{\sqrt{\hat{d}_j \hat{d}_i}}(\Theta_2 e_{j,i}^M \cdot h_j^{(t)})\right) + \alpha h_j^{(0)} \tag{21}$$

$$h_i^{(t+1)} = \Theta_3 h_i^t \tag{22}$$

The GRU operating on graph topology can be formulated as, $$h_i^{(t+1)} = GRU\left(h_i^{(t)}, \{h_j^{(t)}, e_{ji}: j \in N(i), (i, j) \in \varepsilon \leftrightarrow (j, i) \in \varepsilon\}\right) \tag{23}$$

The $\epsilon$ value is 1e-6.

$$\hat{d}_i = \sum\nolimits_{j \in N(i)} \hat{A}_{ij}$$

$\hat{A}_{ij}$ is the degree or node i.
Here, $$h_i^{(t+1)}$$

is the learnt hidden representation of node, i. $\Theta_1$, $\Theta_2$, and $\Theta_3$ are the trainable weight matrices. Here, $\alpha \in (0,1]$ is the teleport (otherwise restart) probability. $f_i$ and $e_{ji}$ denotes the feature vector of node, i and the static edge-feature vector respectively.

Here, the updated hidden state vector $$\left(h_i^{(t+1)}\right)$$

of each node (i) or the node i is computed by transforming the hidden state vector of the node (i), by adding the weighted (by $\alpha$, which controls the information flow), sum-pooled initial hidden state-vector of node, i at each iteration step. The initial hidden state vector of node (i) is determined by each node in the set of neighboring nodes (j) by taking a product of the feature vector of node (i) with a linearly transformed edge-feature vector $$e_{ij}^M$$

with a trainable weight parameter $\Theta_1$ at each iteration step. The gated recurrent neural network is weighted by a factor $(1-\alpha)$. At each iteration step, to leverage information from a larger graph-neighborhood, a Gated recurrent neural network is leverage and it is weighted by, $(1-\alpha)$. In the present embodiment, the gated recurrent neural network takes a previous hidden state of the node (i) and the aggregated normalized neural-message vector from the set of neighbor's nodes as inputs. The normalized message vector from each local-graph neighbor, j is determined by the ratio of the product of the hidden state of the node, j at previous iteration-step, t and the linearly transformed static edge feature vector by the trainable weight matrix, $\Theta_2$ and the square-root of the product of the degree of the sink node, i and the source node, j with the added self-loops respectively. As mentioned previously, a self-added loop for each node comprises an arbitrary edge starting and ending at the node.

The updated hidden state vectors of the plurality of nodes are pooled to calculate the discriminative graph-level vector representation of the molecular graph at step 410 of method 400. The graph-level vector representation is a characteristic representation of the molecular graph.

At step 412, the method includes applying a linear layer function on the discriminative graph-level vector representation to compute the molecular properties.

FIG. 5 is a block diagram of an exemplary computer system 501 for implementing embodiments consistent with the present disclosure. The computer system 501 may be implemented in alone or in combination of components of the system 302 (FIG. 1). Variations of computer system 501 may be used for implementing the devices included in this disclosure. Computer system 501 may comprise a central processing unit ("CPU" or "hardware processor") 502. The hardware processor 502 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD Athlon™, Duron™ or Opteron™, ARM's application, embedded or secure processors, IBM PowerPC™, Intel's® Core, Itanium™, Xeon™, Celeron™ or other line of processors, etc. The processor 502 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc. The processor 502 may be a multi-core multi-threaded processor.

Processor 502 may be disposed in communication with one or more input/output (I/O) devices via I/O interface 503. The I/O interface 503 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth®, cellular (e.g., code-division multiple access (CDMA), high-speed packet access (HSPA+), global system for mobile communications (GSM), long-term evolution (LTE), WIMAX™, or the like), etc.

Using the I/O interface 503, the computer system 501 may communicate with one or more I/O devices. For example, the input device 504 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 505 may be a printer, fax machine, video display (e.g., cathode ray tube (CRT), liquid crystal display (LCD), light-emitting diode (LED), plasma, or the like), audio speaker, etc. In some embodiments, a transceiver 506 may be disposed in connection with the processor 502. The transceiver may facilitate various types of wireless transmission or reception. For example, the transceiver may include an antenna operatively connected to a transceiver chip, providing IEEE 802.11a/b/g/n, Bluetooth®, FM, global positioning system (GPS), 2G/3G HSDPA/HSUPA communications, etc.

In some embodiments, the processor 502 may be disposed in communication with a communication network 508 via a network interface 507. The network interface 507 may communicate with the communication network 508. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 508 may include, without limitation, a direct interconnection, local area network (LAN), wide area network (WAN), wireless network (e.g., using Wireless Application Protocol), the Internet, etc. Using the network interface 507 and the communication network 508, the computer system 501 may communicate with devices 509 and 510. These devices may include, without limitation, personal computer(s), server(s), fax machines, printers, scanners, various mobile devices such as cellular telephones, smartphones, tablet computers, eBook readers (AMAZON KINDLE®, NOOK®, etc.), laptop computers, notebooks, gaming consoles (MICROSOFT XBOX®, NINTENDO DS®, SONY® PLAYSTATION, etc.), or the like. In some embodiments, the computer system 501 may itself embody one or more of these devices.

In some embodiments, the processor 502 may be disposed in communication with one or more memory devices (e.g., RAM 513, ROM 514, etc.) via a storage interface 512. The storage interface may connect to memory devices including, without limitation, memory drives, removable disc drives, etc., employing connection protocols such as serial advanced technology attachment (SATA®), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices may store a collection of programs or database components, including, without limitation, an operating system 516, user interface application 517, user/application data 518 (e.g., any data variables or data records discussed in this disclosure), etc. The operating system 516 may facilitate resource management and operation of the computer system 501. Examples of operating systems include, without limitation, UNIX®, UNIX®-like system distributions (e.g., Berkeley Software Distribution (BSD), FreeBSD®, NetBSD, OpenBSD, etc.), LINUX® distributions (e.g., RED HAT®, UBUNTU®, KUBUNTU®, etc.), IBM® OS/2, MICROSOFT® WINDOWS (XP®, VISTA®/7/8, etc.), GOOGLE™ ANDROID™, BLACKBERRY™ OS, or the like. User interface 517 may facilitate display, execution, interaction, manipulation, or operation of program components through textual or graphical facilities. For example, user interfaces may provide computer interaction interface elements on a display system operatively connected to the computer system 501, such as cursors, icons, check boxes, menus, scrollers, windows, widgets, etc. Graphical user interfaces (GUIs) may be employed, including, without limitation, IBM® OS/2, MICROSOFT® WINDOWS (e.g., Aero, Metro, etc.), UNIX® X-Windows, web interface libraries (e.g., ActiveX™, JAVA®, JAVASCRIPT®, AJAX, HTML, ADOBE® Flash, etc.), or the like.

In some embodiments, computer system 501 may store user/application data 518, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as hand-oriented databases (e.g., using HandStore, Poet, Zope™, etc.). Such databases may be consolidated or distributed, sometimes among various computer systems discussed above. It is to be understood that the structure and operation of any computer or database component may be combined, consolidated, or distributed in any working combination.

Additionally, in some embodiments, (the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

Example Scenario:

To report the full ablation studies on the proposed novel message-passing pipeline variants, for chemical graphs on predicting chemical properties. Publicly accessible Quantum Machine 9 dataset, is leveraged. The dataset comprises approximately 134k molecules that cover a comprehensive set of molecules in chemical science. It contains quantum chemical properties of low tree-width molecular graphs. The dataset consists of druglike organic chemical compounds and accommodates a total of nine substantial atoms.

For each atom entity in a drug-like organic molecule in the Quantum Machine 9 dataset, there exists a variety of characteristic features at hand that forms the basis for the node feature vector in data.x. The static feature representation of the edge connecting two neighboring nodes in the chemical graph forms the basis for data.edgeattributes. The hydrogen atoms are treated as explicit vertices in the chemical graph.

| Illustration of node attributes in the molecular graphs | |
| --- | --- |
| Characteristic Feature | Representation |
| Atom type | one-hot |
| Atomic number | Integer |
| Acceptor | binary |
| Donor | binary |
| Aromatic | binary |
| Hybridization | one-hot or null |
| Number of Hydrogens | integer |

| Illustration of static edge feature attributes | |
| --- | --- |
| Characteristic Feature | Representation |
| Bond type | one-hot |
| Aromatic ring | binary |
| Euclidean distance between nodes | Vector |

For each distinct and unique molecule, DFT simulations are used to configure an appropriate low energy structure and thus atom positions are available. Each model was trained for graph-level-based regression tasks for the Quantum Chemistry property prediction task. Message passing computational steps, T was constrained to be at 3. The set2set mathematical iterations, M was on par with T. Here, all the models were trained by leveraging a random selection of datasets for stochastic gradient descent optimization with the Adaptive Moment Estimation optimizer algorithm with batch size 10.

The number of iterations (epochs) is 100 cycles through the full training dataset. The beginning learning rate was chosen as 1e-3. The learning rate was decayed at 51st epoch by half and maintained it constant in the span of [51; 75] epochs throughout the training and the beginning step size learning rate l decayed to a terminating learning rate 2:5e-4, using a decay factor by 4 in the range [76; 100] epochs. The QM-9 dataset consists of approximately 134K molecules. The validation set comprises 10000 samples. The test set is composed of 10000 samples and the remaining are for the training set. Here, early stopping is implemented on the validation dataset to prevent the model from over-fitting and for model selection. Finally, we evaluate the performance of the model and publish the evaluation metric based totally on the test set. Feature scaling was performed on the target properties to be predicted. Z-score normalization is leveraged to have distribution mean zero and the expectation of the squared deviation to one for each target property. The gradient descent (aka back-propagation) algorithm was run in weight space by updating the parameters according to the gradients of the loss function, the mean squared error between the predicted model outputs and the predetermined DFT properties. The results are reported in MAE metric.

TABLE 1

| Performance comparison of the proposed methods (left) with the baseline MPNN algorithm on validation dataset | | | |
| --- | --- | --- | --- |
| | Disclosed Method | Baseline | |
| Target | Alg-1 | enns2s | enns2sens5 |
| mu | 0.015 | 0.3 | 0.2 |
| alpha | 0.091 | 0.92 | 0.68 |
| HOMO | 0.04 | 0.99 | 0.74 |
| LUMO | 0.048 | 0.87 | 0.65 |
| gap | 0.058 | 1.6 | 1.23 |
| R2 | 0.025 | 0.44 | 0.14 |
| ZPVE | 0.022 | 1.27 | 1.1 |
| U0 | 0.064 | 0.45 | 0.33 |
| U | 0.042 | 0.45 | 0.34 |
| H | 0.089 | 0.39 | 0.3 |
| G | 0.045 | 0.44 | 0.34 |
| Cv | 0.031 | 0.8 | 0.62 |
| Omega | 0.059 | 0.19 | 0.15 |

TABLE 2

| Performance comparison of the proposed methods (left) with the baseline MPNN algorithm on test dataset. | | | |
| --- | --- | --- | --- |
| | Disclosed method | Baseline | |
| Target | Alg-1 | enns2s | enns2sens5 |
| mu | 0.016 | 0.3 | 0.2 |
| alpha | 0.094 | 0.92 | 0.68 |
| HOMO | 0.039 | 0.99 | 0.74 |
| LUMO | 0.049 | 0.87 | 0.65 |
| gap | 0.059 | 1.6 | 1.23 |
| R2 | 0.027 | 0.44 | 0.14 |
| ZPVE | 0.026 | 1.27 | 1.1 |
| U0 | 0.068 | 0.45 | 0.33 |
| U | 0.044 | 0.45 | 0.34 |
| H | 0.092 | 0.39 | 0.3 |
| G | 0.047 | 0.44 | 0.34 |
| Cv | 0.034 | 0.8 | 0.62 |
| Omega | 0.062 | 0.19 | 0.15 |

Graph Regression Task: Here, Error Ratio is the metric reported for the graph-based based regression task. It is defined as the fraction of the MAE of the model's performance with the known approximate of chemical accuracy for that target property. Chemical accuracy approximates for every target property is reported in previous works. A model with an error ratio lesser than one has successfully attained chemical accuracy for that particular target property. The mean absolute error of the proposed unifying variants of MPNNs models will be computed as (Error Ratio)×(Chemical Accuracy). Here in this work, unless if specified, the tables display results of models trained for predicting all the targets in contrast to training a unique and distinct model to predict the targets individually as reported in previous works. A previous comparative study of various diverse known existing ML models was carried out in the literature on QM9 dataset. Here in these embodiments, identical train, validation, and test split were utilized. In table 1, and 2, the performance of the baseline MPNN variant, are displayed (represented with enn-s2s and the corresponding ensemble represented with enn-s2sens5). The results are reported previously in terms of error ratio. Overall, the proposed unifying variants of MPNN models realizes chemical accuracy on each of 13 target properties and attains the best performance on all 13 targets. The results are reported for both validation and test dataset. It suggests that the model is well regularized to avoid over-fitting.

For further comparisons with the literature, here a comparison with baseline methods on test dataset is reported, refer Table 3. MAE is the metric reported. It presents the results of six state-of-the-art models, SchNet, PhysNet, provably powerful graph networks, MEGNet, Cormorant, and DimeNet. The state of the art performance on the prediction of all the 13 targets is demonstrated on QM9 dataset.

TABLE 3

Performance comparision of the proposed method (right) with the baseline
algorithms on test dataset. MAE is the metric reported.

| Target | Baseline | | | | | | Baseline |
| | PPGN | S-N | P-N | M-N | C-N | D-N | Alg-1 |
|---|---|---|---|---|---|---|---|
| G | 36.4 | 14 | 9.4 | 12 | — | 8.98 | 0.0021 |
| H | 36.3 | 14 | 8.42 | 12 | — | 8.11 | 0.0039 |
| HOMO | 40.3 | 41 | 32.9 | 43 | 36 | 27.8 | 0.0016 |
| LUMO | 32.7 | 34 | 24.7 | 44 | 36 | 19.7 | 0.0021 |
| R2 | 0.592 | 0.073 | 0.765 | 0.302 | 0.673 | 0.331 | 0.0324 |
| U | 36.8 | 14 | 8.15 | 12 | — | 7.89 | 0.0018 |
| U0 | 36.8 | 14 | 8.15 | 12 | — | 8.02 | 0.0029 |
| ZPVE | 3.12 | 1.7 | 1.39 | 1.43 | 1.98 | 1.29 | 3.12E−05 |
| Alpha | 0.131 | 0.235 | 0.0615 | 0.081 | 0.092 | 0.0469 | 0.0094 |
| Gap | 60 | 63 | 42.5 | 66 | 60 | 34.8 | 0.0025 |
| Mu | 0.047 | 0.033 | 0.0529 | 0.05 | 0.13 | 0.0286 | 0.0016 |

Here, the objective of the disclosed embodiments is to predict properties that relate to the electronic properties of the molecules pre-determined by the computational Density Functional Theory (DFT) quantum-mechanical simulations, HOMO, $\varepsilon_{HOMO}$ (eV) and LUMO $\varepsilon_{LUMO}$ (eV). Then, the electron energy gap ($\Delta_\varepsilon$ (eV)). $\varepsilon_{HOMO\text{-}\varepsilon LUMO}$ is described as the electron energy gap. For further comparisons with the literature. Deriving neural architectures from sequence and graph kernels is looked upon in great detail. It proposes kernels over combinatorial structures such as graphs, and the model is a Weisfeiler-Lehman NN, with 4 recurrent iterations and it performs 2-nd order random walk. The other baseline methods are Neural Finger-print, which is a 4-layer convolutional neural network and Embedded Loopy Belief Propagation. It is a recurrent neural network architecture with 4 recurrent iterations. These algorithms are implemented for the given QM9 dataset. Table 4 and 5 shows disclosed model sets the benchmark as compared to against various baselines. The proposed models are well-regularized with proper hyperparameter tuning.

TABLE 4

Performance comparison of then proposed methods
(left) with the baseline's variants(right) on
validation dataset. RMSE is the metrics reported.

| Target | Disclosed method | Baseline | | |
| | Alg-1 | WLNN | NFP | ELBP |
|---|---|---|---|---|
| HOMO | 0.0023 | 0.0026 | 0.0099 | 0.0032 |
| LUMO | 0.0028 | 0.0026 | 0.019 | 0.0033 |
| gap | 0.0034 | 0.0035 | 0.0202 | 0.0045 |

TABLE 5

Performance comparison of the proposed methods
(left) with the baseline's variants(right)
on test dataset. RMSE is the metrics reported.

| Target | Disclosed method | Baseline | | |
| | Alg-1 | WLNN | NFP | ELBP |
|---|---|---|---|---|
| HOMO | 0.0021 | 0.0037 | 0.0067 | 0.0038 |
| LUMO | 0.003 | 0.2717 | 0.2684 | 0.2715 |
| gap | 0.0034 | 0.514 | 0.5094 | 0.5139 |

Sequence (SMILES) based property prediction task: Prior work on drug molecules property prediction task was formulated on a string representation of chemical compounds. In chemo-informatics includes the SMILES representation of molecules. SMILES is an acronym for the Simplified molecular-input line-entry system. These models leverage SMILES representation, a linear string notation to represent the molecular structures. Graph representations of the molecules can be generated using SMILES strings through a deterministic mapping. In natural language processing (NLP), in specific the input to the language model is an ordered list of a solitary letters, strings, or words if given an input sequence of text. The model predicts the probability of each and the predicted output is fed as input to in succession to give rise to the succeeding. Here, the SMILES format which is a simple language with an appropriate grammar rules is leveraged to encode chemical graphs concisely as human-readable linguistic construct strings. Smiles is a formal grammar that express molecules by leveraging alphabet of unique and distinct characters and with every nonhydrogen atom is represented by its atomic symbol surrounded. Atoms are represented by their atomic symbols for example c and C for aromatic and aliphatic carbon atoms and O for oxygen. Single, double, triple, and aromatic bonds are described by —, = and # and : symbols and the branches are described by encircled them in parentheses. Here, several state-of-the-art machine translation algorithms solved together with the DFT property prediction (regression) task. The weights of the network are updated with respect to the combined loss of reconstruction accuracy as well as the regression-based MAE loss. The algorithms leveraged are VAE-Bahdanau Attention and Seq2Seq-Bidirectional-Bahdanau Attention-Scheduled Sampling-based algorithms. Thereafter an additional feed-forward network is utilized as a property prediction module by operating on the latent space.

TABLE 4

Comparison of the disclosed methods (left) on test
dataset with sequence based machine translation
algorithms. RMSE is the metrics reported.

| Target | Disclosed method | Baseline | |
| | Alg-1 | VAEBA | Seq2Seq-BA-SS |
|---|---|---|---|
| HOMO | 0.00217 | 0.01914 | 0.02214 |
| LUMO | 0.00305 | 0.02757 | 0.047 |
| gap | 0.00349 | 0.02697 | 0.04832 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for molecular property prediction, comprising:

accessing, via one or more hardware processors, a database comprising a plurality of molecular graphs associated with a plurality of molecules and a plurality of labels indicative of chemical properties of the plurality of the molecular graphs, wherein a molecular graph of the plurality of molecular graphs comprises a plurality of nodes and a plurality of edges connecting a plurality of neighboring nodes;

learning, via the one or more hardware processors, a mapping from the plurality of molecular graphs to a set of labels by a molecular property prediction neural network function to prognosticate the chemical properties of the molecular graph from amongst the plurality of molecular graphs, wherein predicting the properties of the molecular graph comprises computing a graph-level vector representation of the molecular graph using an Edge-Information Fused Message Passing Neural Network (EI-MPNN), and wherein computing the graph-level vector representation for the molecular graph comprises:

computing an incoming aggregated message vector for each node (i) of the plurality of nodes of the molecular graph, wherein the incoming aggregated message vector for each node (i) is computed based on a plurality of encoded messages received from a set $$(h_j^t)$$

of neighboring nodes (j) of each node (i), wherein each encoded message vector is generated by fusing a node information and a connecting edge information of the set $$(h_j^t)$$

of neighboring nodes (j) of the node (i), wherein each of the plurality of encoded messages comprises a normalized neural-message vector, wherein the normalized neural-message vector from each neighboring node of the set $$\left(h_j^t\right)$$

of neighboring nodes (j) is determined by a ratio of a summation of hidden state vector of each node (i) in the set $$\left(h_j^t\right)$$

of neighboring nodes (j), a linearly transformed static edge feature vector altered by a second trainable weight matrix, $\Theta_2$, a square-root of a product of a degree of each node (i), and the set $$\left(h_j^t\right)$$

of neighboring nodes (j) with added self-loops,
   wherein the added self-loops include a self-loop of each node (i) comprising an arbitrary edge that starts and terminates at a same node that is considered in calculating the degree of each node (i),
   wherein an edge $$e_{j,i}^M$$

pertains to the self-loop of the node (i), and
   a node-wise formulation is expressed as:

$$h_i' = \Gamma_\Theta\!\left((1+\epsilon)W_0 h_i + \sum_{j\in N(i)} \frac{1}{\sqrt{\hat{d}_j \hat{d}_i}}\left(h_j + W_1 e_{j,i}^M\right)\right),$$

wherein $h_i$ is a representation vector of the node (i) at a previous layer, $\hat{d}_i$ is the degree of the node (i) with the added self-loop, $\hat{d}_j$ is the degree of the node (j), $$\sum_{j\in N(i)}$$

is aggregation of neural-information embedded messages over a local one-hop neighborhood of the node, $W_0$ & $W_1$ are a trainable weight matrices that apply a linear transformation to feature and static edge feature vectors respectively, $\delta_\Theta$ denotes a neural network comprising a multilayer perceptron (MLP) parameterized by $\Theta$, $\epsilon$ denotes an epsilon value, $e^{-7}$;
   computing iteratively an updated hidden state vector of each node in a plurality of pre-determined number of iterations from the incoming aggregated message vector and a hidden state of the node, wherein the hidden state of the node is obtained from a previous iteration; and
   calculating a discriminative graph-level vector representation by pooling the updated hidden state vectors of the plurality of nodes, wherein the graph level vector representation is a characteristic representation of the molecular graph; and
applying a linear layer function on the discriminative graph-level vector representation to compute the properties of the molecular graph, via the one or more hardware processors, wherein the EI-MPNN comprises an Edge-Conditioned Identity Mapping Convolution Network (EC-IMCN) which aids in inductive learning tasks by incorporating edge-information of a graph topology, prevents over-smoothing of learnable low-level representations for nodes with valency and prevents diffusion of node embeddings to a corresponding local sizeable-graph neighborhood.

2. The processor implemented method of claim 1, wherein the updated hidden state vector $$\left(h_i^{(t+1)}\right)$$

of each node (i) IS Computed by transforming the previous iteration step, hidden state vector $$\left(h_i^t\right)$$

of each node (i) by using a reed-forward neural-network function $\Gamma_\Theta$, and wherein the input to the feed-forward neural-network function comprises a summation of a linear transformation of the node (i) hidden state vector $$\left(h_i^t\right)$$

with a first trainable weight matrix, $\Theta_1$ and the aggregated-message vector from the set $$\left(h_j^t\right)$$

of neighboring nodes (j).

3. The processor implemented method of claim 1, wherein the updated hidden state vector $$\left(h_i^{(t+1)}\right)$$

of each node (i) is computed by transforming the previous hidden state vector of the node (i) by performing a summation operation on a linear transformation of the node (i) hidden state vector with the trainable weight matrix, $\Theta_1$ and an aggregated neural-message vector from the set $$\left(h_j^t\right)$$

of neighboring nodes (j).

4. The processor implemented method of claim 3, wherein the aggregated neural-message vector is determined by computing a product of transformed strength of an identity mapping to allow a gated aggregated neural-information flow from the set $$\left(h_j^t\right)$$

of neighboring nodes (j).

5. The processor implemented method of claim 4, wherein the gated aggregated neural-information flow is determined by a summation of a weighted product of a less-discriminative aggregated message-vector $$\sum_{j \in N(i)} h_j^t \Omega_\Lambda\left(e_{ij}^M\right)$$

with $(1-\alpha)$ and a weighted product of an initial residual aggregated neural-message vector $$\sum_{j \in N(i)} h_j^{(0)} \Omega_\Lambda\left(e_{ij}^M\right)$$

with $\alpha$(a learnable gating scalar value), wherein, a less-discriminative and the initial residual aggregated neural-message vector are determined by a sum-message pooling operation, wherein a less-discriminative message-vector is determined by a product of the transformed edge-vector with the neighboring node (j), hidden state, and is described by $$h_j \Omega_\Lambda\left(e_{ij}^M\right),$$

wherein an initial residual neural-message vector is determined by a product of the transformed edge-vector with the neighboring node (j), feature vector, and is described by $$h_j^0 \Omega_\Lambda\left(e_{ij}^M\right),$$

wherein, the transformed edge-vector comprises the output of a feed-forward neural network function, $\Omega_\Lambda$ which takes as input the static-edge feature vector, $$e_{ij}^M,$$

wherein an aggregated message-vector $m_{N(i)}$ is determined by the sum-message pooling operation on a local-graph neighborhood as, $$m_{N(i)} =$$

$$\left((1 - \alpha)\sum_{j \in N(i)} h_j^t \Omega_\Lambda\left(e_{ij}^M\right) + \alpha \sum_{j \in N(i)} h_j^{(0)} \Omega_\Lambda\left(e_{ij}^M\right)\right)((1 - \beta)I + \beta W_2),$$

and wherein $W_1$ and $W_2$ are the trainable weight matrices, $$e_{ij}^M$$

denotes a static feature vector of an edge connecting an neighboring nodes, (j, i), $$h_j^{(0)}$$

represents a feature information vector of the node (i), $\alpha$ models strength of the initial residual aggregated neural-message vector from local-graph neighbors, $$\sum_{j \in N(i)} h_j^{(0)} \Omega_\Lambda\left(e_{ij}^M\right),$$

$\alpha$ & $(1-\alpha)$ serves as gating vectors by combining information from a less-discriminative aggregated single message-vector $$\sum_{j \in N(i)} h_j^t \Omega_\Lambda\left(e_{ij}^M\right)$$

with the initial residual aggregated neural-message vector, $\beta$ models strength of a identity mapping to a corresponding learnable weight matrix, W2, $\Omega_\Lambda$ denotes a multi-layer perceptron, parameterized by $\Lambda$, and 1 is an identity matrix.

6. The processor implemented method of claim 1, wherein the updated hidden state vector $$\left(h_i^{(r+1)}\right)$$

of each node (i) is computed by transforming the hidden state vector of the node (i), wherein transforming the hidden state vector of the node (i) comprises adding a weighted and sum-pooled initial hidden state-vector of the node (i) at each iteration step, and wherein the initial hidden state vector of node (i) is determined by each node (i) in the set $$\left(h_j^t\right)$$

of neighboring nodes (j) by taking a product of the feature vector of node (i) with a linearly transformed edge-feature vector $$e_{ij}^M$$

with a trainable weight parameter $\Theta_1$ at each iteration step, and wherein the gated recurrent neural network is weighted by a factor $(1-\alpha)$, and wherein the gated recurrent neural network takes a previous hidden state of the node (i) and an aggregated normalized neural-message vector from the set $$\left(h_j^t\right)$$

of neighboring nodes (i) as inputs, and wherein the normalized message vector from each neighboring node is determined by a ratio of a product of hidden representation of each local-graph neighbor node (j) at previous iteration-step (t) and the linearly transformed static edge feature vector by the trainable weight matrix $\Theta_2$, and the square-root of the product of the degree of the node (i) and each neighboring node (j) with the added self-loops, and wherein a self-added loop for each node comprises an arbitrary edge starting and ending at the node.

7. A system for molecular property prediction, comprising:

a memory storing instructions;

one or more communication interfaces; and one or more hardware processors coupled to the memory via the one or more communication interfaces, wherein the one or more hardware processors are configured by the instructions to:

access a database comprising a plurality of molecular graphs associated with a plurality of molecules and a plurality of labels indicative of chemical properties of the plurality of the molecular graphs, wherein a molecular graph of the plurality of molecular graphs comprises a plurality of nodes and the plurality of edges connecting the plurality of neighboring nodes;

learn a mapping from the plurality of molecular graphs to the set of labels by a molecular property prediction neural network function to prognosticate the chemical properties of the molecular graph from amongst the plurality of molecular graphs, wherein predicting the properties of the molecular graph comprises computing a graph-level vector representation of the molecular graph using an Edge-Information Fused Message Passing Neural Network (EI-MPNN), and wherein to computing the graph-level vector representation for the molecular graph, the one or more hardware processors are configured by the instructions to:

compute an incoming aggregated message vector for each node (i) of the plurality of nodes of the molecular graph, wherein the incoming aggregated message vector for each node (i) is computed based on a plurality of encoded messages received from a set $$\left(h_j^t\right)$$

of neighboring nodes (j) of each node (i), wherein each encoded message vector is generated by fusing a node information and a connecting edge information of the set $$\left(h_j^t\right)$$

of neighboring nodes (j) of the node (i), wherein each of the plurality of encoded messages comprises a normalized neural-message vector, wherein the normalized neural-message vector from each neighboring node of the set $$\left(h_j^t\right)$$

of neighboring nodes (j) is determined by a ratio of a summation of hidden state vector of each node (i) in the set $$\left(h_j^t\right)$$

of neighboring nodes (j), a linearly transformed static edge feature vector altered by a second trainable weight matrix, $\Theta_2$, a square-root of a product of a degree of each node (i), and the set $$\left(h_j^t\right)$$

of neighboring nodes (j) with added self-loops, wherein the added self-loops include a self-loop of each node (i) comprising an arbitrary edge that starts and terminates at a same node that is considered in calculating the degree of each node (i), wherein an edge $$e_{j,i}^M$$

pertains to the self-loop of the node (i), and a node-wise formulation is expressed as:

$$h_i' = \Gamma_\Theta\left((1 + \epsilon)W_0 h_i + \sum\nolimits_{j \in N(i)} \frac{1}{\sqrt{\hat{d}_j \hat{d}_i}}\left(h_j + W_1 e_{j,i}^M\right)\right),$$

wherein $h_i$ is a representation vector of the node (i) at a previous layer, $d_i$ is the degree of the node (i) with the added self-loop, $d_j$ is the degree of the node (j), $$\sum\nolimits_{j \in N(i)}$$

is aggregation or neural-information embedded messages over a local one-hop neighborhood of the node, $W_0$ & $W_1$ are a trainable weight matrices that apply a linear transformation to feature and static edge feature vectors respectively, $\Gamma_\Theta$ denotes a neural network comprising a multilayer perceptron (MLP) parameterized by $\Theta$, $\epsilon$ denotes an epsilon value, $e^{-7}$;

compute iteratively an updated hidden state vector of each node in a plurality of pre-determined number of iterations from the incoming aggregated message vector and a hidden state of the node, wherein the hidden state of the node is obtained from a previous iteration; and calculate a discriminative graph-level vector representation by pooling the updated hidden state vectors of the plurality of nodes, wherein the graph level vector representation is a characteristic representation of the molecular graph; and apply a linear layer function on the discriminative graph-level vector representation to compute the properties of the molecular graph, wherein the EI-MPNN comprises an Edge-Conditioned Identity Mapping Convolution Network (EC-IMCN) which aids in inductive learning tasks by incorporating edge-information of a graph topology, prevents over-smoothing of learnable low-level representations for nodes with valency and pre vents diffusion of node embeddings to a corresponding local sizeable-graph neighborhood.

8. The system of claim 7, wherein the one or more hardware processors are configured by the instructions to compute the updated hidden state vector $$\left(h_i^{(t+1)}\right)$$

of each node (i) by transforming the previous iteration step, hidden state vector $$\left(h_i^t\right)$$

of each node (i) by using a feed-forward neural-network function $\Gamma_\Theta$, and wherein the input to the feed-forward neural-network function comprises a summation of a linear transformation of the node (i) hidden state vector $$\left(h_i^t\right)$$

with a first trainable weight matrix, $\Theta_1$ and the aggregated-message vector from the set $$\left(h_j^t\right)$$

of neighboring nodes (j).

9. The system of claim 7, wherein the updated hidden state vector $$\left(h_i^{(t+1)}\right)$$

of each node (i) is computed by transforming the previous hidden state vector of the node (i) by performing a summation operation on a linear transformation of the node (i) hidden state vector with the trainable weight matrix, $\Theta_1$ and an aggregated neural-message vector from the set $$\left(h_j^t\right)$$

of neighboring nodes (j).

10. The system of claim 9, wherein to determine the aggregated neural-message vector, the one or more hardware processors are configured by the instructions to compute a product of transformed strength of an identity mapping to allow a gated aggregated neural-information flow from the set $$\left(h_j^t\right)$$

of neighboring nodes (j).

11. The system of claim 10, wherein to determine the gated aggregated neural-information flow, the one or more hardware processors are configured by the instructions to perform a summation of a weighted product of a less-discriminative aggregated message-vector $$\sum_{j \in N(i)} h_j^t \Omega_\Lambda\left(e_{ij}^M\right)$$

with (1−α) ana a weighted product of an initial residual aggregated neural-message vector $$\sum_{j \in N(i)} h_j^{(0)} \Omega_\Lambda\left(e_{ij}^M\right)$$

with α(a learnable gating scalar value), wherein, a less-discriminative and the initial residual aggregated neural-message vector are determined by a sum-message pooling operation, wherein a less-discriminative message-vector is determined by a product of the transformed edge-vector with the neighboring node (j), hidden state, and is described by $$h_j \Omega_\Lambda\left(e_{ij}^M\right),$$

wherein an initial residual neural-message vector is determined by a product of the transformed edge-vector with the neighboring node (j), feature vector, and is described by $$h_j^0 \Omega_\Lambda\left(e_{ij}^M\right),$$

wherein, the transformed edge-vector comprises the output of a feed-forward neural network function, $\Omega_\Lambda$ which takes as input the static-edge feature vector, $$e_{ij}^M,$$

wherein an aggregated message-vector $m_{N(i)}$ is determined by the sum-message pooling operation on a local-graph neighborhood as, $$m_{N(i)} =$$
$$\left((1-\alpha)\sum_{j \in N(i)} h_j^t \Omega_\Lambda\left(e_{ij}^M\right) + \alpha \sum_{j \in N(i)} h_j^{(0)} \Omega_\Lambda\left(e_{ij}^M\right)\right)((1-\beta)I + \beta W_2),$$

and wherein $W_1$ and $W_2$ are the trainable weight matrices, $$e_{ij}^M$$

denotes a static feature vector of an edge connecting an neighboring nodes, $$(j, i), h_j^{(0)}$$

represents a feature information vector of the node (i), $\alpha$ models strength of the initial residual aggregated neural-message vector from local-graph neighbors, $$\sum_{j \in N(i)} h_j^{(0)} \Omega_\Lambda(e_{ij}^M),$$

$\alpha$ & $(1-\alpha)$ serves as gating vectors by combining information from a less-discriminative aggregated single message-vector $$\sum_{j \in N(i)} h_j^t \Omega_\Lambda(e_{ij}^M)$$

with the initial residual aggregated neural-message vector, $\beta$ models strength of a identity mapping to a corresponding learnable weight matrix, W2, $\Omega_\Lambda$ denotes a multi-layer perceptron, parameterized by $\Lambda$, and l is an identity matrix.

12. The system of claim 7, wherein the updated hidden state vector $$(h_i^{(t+1)})$$

of each node (i) is computed by transforming the hidden state vector of the node (i), wherein transforming the hidden state vector of the node (i) comprises adding a weighted and sum-pooled initial hidden state-vector of the node (i) at each iteration step, and wherein the initial hidden state vector of node (i) is determined by each node (i) in the set $$h_j^t$$

of neighboring nodes (j) by taking a product of the feature vector of node (i) with a linearly transformed edge-feature vector $$e_{ij}^M$$

with a trainable weight parameter $\Theta_1$ at each iteration step, and
  wherein the gated recurrent neural network is weighted by a factor $(1-\alpha)$, and
  wherein the gated recurrent neural network takes a previous hidden state of the node (i) and an aggregated normalized neural-message vector from the set $$h_j^t$$

of neighboring nodes (j) as inputs, and
  wherein the normalized message vector from each neighboring node is determined by a ratio of a product of hidden representation of each local-graph neighbor node (j) at previous iteration-step (t) and the linearly transformed static edge feature vector by the trainable weight matrix $\Theta_2$, and the square-root of the product of the degree of the node (i) and each neighboring node (j)

with the added self-loops, and wherein a self-added loop for each node comprises an arbitrary edge starting and ending at the node.

13. One or more non-transitory machine-readable information storage mediums comprising one or more instructions which when executed by one or more hardware processors cause:
  accessing, via one or more hardware processors, a database comprising a plurality of molecular graphs associated with a plurality of molecules and a plurality of labels indicative of chemical properties of the plurality of the molecular graphs, wherein a molecular graph of the plurality of molecular graphs comprises a plurality of nodes and a plurality of edges connecting a plurality of neighboring nodes;
  learning, via the one or more hardware processors, a mapping from the plurality of molecular graphs to a set of labels by a molecular property prediction neural network function to prognosticate the chemical properties of the molecular graph from amongst the plurality of molecular graphs, wherein predicting the properties of the molecular graph comprises computing a graph-level vector representation of the molecular graph using an Edge-Information Fused Message Passing Neural Network (EI-MPNN), and wherein computing the graph-level vector representation for the molecular graph comprises:
    computing an incoming aggregated message vector for each node (i) of the plurality of nodes of the molecular graph,
    wherein the incoming aggregated message vector for each node (i) is computed based on a plurality of encoded messages received from a set $$h_j^t$$

of neighboring nodes (j) of each node (i),
    wherein each encoded message vector is generated by fusing a node information and a connecting edge information of the set $$h_j^t$$

of neighboring nodes (j) of the node (i),
    wherein each of the plurality of encoded messages comprises a normalized neural-message vector,
    wherein the normalized neural-message vector from each neighboring node of the set $$h_j^t$$

of neighboring nodes (j) is determined by a ratio of a summation of hidden state vector of each node (i) in the set $$h_j^t$$

of neighboring nodes (j), a linearly vector of each node (i) in the set transformed static edge feature vector altered by a second trainable weight matrix, $\Theta_2$, a square-root of a product of a degree of each node (i), and the set $$h_j^t$$

of neighboring nodes (j) with added self-loops, wherein the added self-loops include a self-loop of each node (i) comprising an arbitrary edge that starts and terminates at a same node that is considered in calculating the degree of each node (i), wherein an edge $$e_{ij}^M$$

pertains to the self-loop of the node (i), and a node-wise formulation is expressed as:

$$h_i' = \Gamma_\Theta\left( (1+\epsilon)W_0 h_i + \sum_{j\in N(i)} \frac{1}{\sqrt{\hat{d}_j\hat{d}_i}}\left(h_j + W_1 e_{j,i}^M\right) \right),$$

wherein $h_i$ is a representation vector of the node (i) at a previous layer, $d_i$ is the degree of the node (i) with the added self-loop, $d_j$ is the degree of the node (j), $$\sum_{j\in N(i)}$$

aggregation of neural-information embedded messages over a local one-hop neighborhood of the node, $W_0$ & $W_1$ are a trainable weight matrices that apply a linear transformation to feature and static edge feature vectors respectively, $\delta_\Theta$ denotes a neural network comprising a multilayer perceptron (MLP) parameterized by $\Theta$, $\epsilon$ denotes an epsilon value, $e^{-7}$;

computing iteratively an updated hidden state vector of each node in a plurality of pre-determined number of iterations from the incoming aggregated message vector and a hidden state of the node, wherein the hidden state of the node is obtained from a previous iteration; and calculating a discriminative graph-level vector representation by pooling the updated hidden state vectors of the plurality of nodes, wherein the graph level vector representation is a characteristic representation of the molecular graph; and applying a linear layer function on the discriminative graph-level vector representation to compute the properties of the molecular graph, via the one or more hardware processors, wherein the EI-MPNN comprises an Edge-Conditioned Identity Mapping Convolution Network (EC-IMCN) which aids in inductive learning tasks by incorporating edge-information of a graph topology, prevents over-smoothing of learnable low-level representations for nodes with valency and prevents diffusion of node embeddings to a corresponding local sizeable-graph neighborhood.

14. The one or more non-transitory machine readable information storage mediums of claim 13, wherein the updated hidden state $$\left(h_i^{(t+1)}\right)$$

of each node (i) is computed by transforming the previous iteration step, hidden state vector $$\left(h_i^t\right)$$

of each node (i) by using a feed-forward neural-network function $\Gamma_\Theta$, and wherein the input to the feed-forward neural-network function comprises a summation of a linear transformation of the node (i) hidden state vector $$\left(h_i^t\right)$$

with a list trainable weight matrix, $\Theta_1$ and the aggregated-message vector from the set $$\left(h_j^t\right)$$

of neighboring nodes (j).

15. The one or more non-transitory machine readable information storage mediums of claim 13, wherein the updated hidden state vector $$\left(h_i^{(t+1)}\right)$$

of each node (i) is computed by transforming the previous hidden state vector of the node (i) by performing a summation operation on a linear transformation of the node (i) hidden state vector with the trainable weight matrix, $\Theta_1$ and an aggregated neural-message vector from the set $$\left(h_j^t\right)$$

of neighboring nodes (j).

16. The one or more non-transitory machine readable information storage mediums of claim 15, wherein the aggregated neural-message vector is determined by computing a product of transformed strength of an identity mapping to allow a gated aggregated neural-information flow from the set $$\left(h_j^t\right)$$

of neighboring nodes (j).

17. The one or more non-transitory machine readable information storage mediums of claim 16, wherein the gated aggregated neural-information flow is determined by a summation of a weighted product of a less-discriminative aggregated message-vector $$\sum_{j \in N(i)} h_j^t \Omega_\Lambda(e_{ij}^\mathcal{M})$$

with $(1-\alpha)$ and a weighted product of an initial residual aggregated neural-message vector $$\sum_{j \in N(i)} h_j^{(0)} \Omega_\Lambda(e_{ij}^\mathcal{M})$$

with $\alpha$(a learnable gating scalar value),
  wherein, a less-discriminative and the initial residual aggregated neural-message vector are determined by a sum-message pooling operation,
  wherein a less-discriminative message-vector is determined by a product of the transformed edge-vector with the neighboring node (j), hidden state, and is described by $$h_j \Omega_\Lambda(e_{ij}^\mathcal{M}),$$

wherein an initial residual neural-message vector is determined by a product of the transformed edge-vector with the neighboring node (j), feature vector, and is described by $$h_j^0 \Omega_\Lambda(e_{ij}^\mathcal{M}),$$

wherein, the transformed edge-vector comprises the output of a feed-forward neural network function, $\Omega_\Lambda$ which takes as input the static-edge feature vector, $$e_{ij}^\mathcal{M},$$

wherein an aggregated message-vector $m_{N(i)}$ is determined by the sum-message pooling operation on a local-graph neighborhood as, $$m_{N(i)} =$$
$$\left( (1-\alpha) \sum_{j \in N(i)} h_j^t \Omega_\Lambda(e_{ij}^\mathcal{M}) + \alpha \sum_{j \in N(i)} h_j^{(0)} \Omega_\Lambda(e_{ij}^\mathcal{M}) \right)((1-\beta)I + \beta W_2),$$

and
  wherein $W_1$ and $W_2$ are the trainable weight matrices, $$e_{ij}^\mathcal{M}$$

denotes a static feature vector of an edge connecting an neighboring nodes, (j, i), $$h_j^{(0)}$$

represents a feature information vector of the node (i), $\alpha$ models strength of the initial residual aggregated neural-message vector from local-graph neighbors, $$\sum_{j \in N(i)} h_j^{(0)} \Omega_\Lambda(e_{ij}^\mathcal{M}),$$

$\alpha$ & $(1-\alpha)$ serves as gating vectors by combining information from a less-discriminative aggregated single message-vector $$\sum_{j \in N(i)} h_j^t \Omega_\Lambda(e_{ij}^\mathcal{M})$$

with the initial residual aggregated neural-message vector, $\beta$ models strength of a identity mapping to a corresponding learnable weight matrix, W2, $\Omega_\Lambda$ denotes a multi-layer perceptron, parameterized by $\Lambda$, and 1 is an identity matrix.

* * * * *